(12) United States Patent
Talts et al.

(10) Patent No.: US 11,446,334 B2
(45) Date of Patent: Sep. 20, 2022

(54) USE OF TERM AMNIOTIC FLUID CELLS FOR THE TREATMENT OF ACUTE AND CHRONIC RESPIRATORY DISEASES

(71) Applicant: Amniotics AB, Lund (SE)

(72) Inventors: Jan Talts, Staffanstorp (SE); Niels-Bjarne Woods, Furulund (SE); Kare Engkilde, Værløse (DK); Marcus Larsson, Bjarred (SE)

(73) Assignee: AMNIOTICS AB, Lund (SE)

( * ) Notice: Subject to any disclaimer, the term of this patent is extended or adjusted under 35 U.S.C. 154(b) by 0 days.

(21) Appl. No.: 17/646,539

(22) Filed: Dec. 30, 2021

(65) Prior Publication Data
US 2022/0118023 A1    Apr. 21, 2022

Related U.S. Application Data

(63) Continuation of application No. PCT/SE2020/050994, filed on Oct. 16, 2020.

(60) Provisional application No. 62/923,187, filed on Oct. 18, 2019.

(30) Foreign Application Priority Data

Oct. 18, 2019    (SE) .................................... 1930338-7
Mar. 26, 2020    (SE) .................................... 2030100-8
Mar. 26, 2020    (SE) .................................... 2030101-6

(51) Int. Cl.
| *A61K 35/50* | (2015.01) |
| *A61K 35/28* | (2015.01) |
| *A61P 11/00* | (2006.01) |
| *C12N 5/0775* | (2010.01) |

(52) U.S. Cl.
CPC .............. *A61K 35/28* (2013.01); *A61K 35/50* (2013.01); *A61P 11/00* (2018.01); *C12N 5/0668* (2013.01)

(58) Field of Classification Search
None
See application file for complete search history.

(56) References Cited

U.S. PATENT DOCUMENTS

| | | | |
|---|---|---|---|
| 4,308,875 A | 1/1982 | Young | |
| 4,567,882 A | 2/1986 | Heller | |
| 4,787,894 A | 11/1988 | Turnbull | |
| 5,019,039 A | 5/1991 | Anderson | |
| 5,048,530 A | 9/1991 | Hurwitz | |
| 5,100,387 A | 3/1992 | Ng | |
| 5,395,379 A | 3/1995 | Deutchman et al. | |
| 5,494,044 A | 2/1996 | Sundberg | |
| 5,951,497 A | 9/1999 | Wallace et al. | |
| 6,378,523 B1 | 4/2002 | Christopher | |
| 6,461,628 B1 | 10/2002 | Blanchard et al. | |
| 6,479,064 B1 | 11/2002 | Atala | |
| 6,506,574 B1 | 1/2003 | Rambhatla et al. | |
| 6,733,433 B1 | 5/2004 | Fell | |
| 7,255,879 B2 | 8/2007 | Hariri | |
| 7,311,905 B2 | 12/2007 | Hariri | |
| 7,596,385 B2 | 9/2009 | Aghvami et al. | |
| 7,638,141 B2 | 12/2009 | Hariri | |
| 7,682,803 B2 | 3/2010 | Paludan et al. | |
| 7,802,574 B2 | 9/2010 | Schultz | |
| 7,914,779 B2 | 3/2011 | Hariri | |
| 8,987,203 B2 | 3/2015 | Van Leeuwen et al. | |
| 9,868,939 B2 | 1/2018 | Slukvin et al. | |
| 10,073,096 B2 | 9/2018 | Lakshmipathy et al. | |
| 10,143,448 B2 | 12/2018 | Brunner | |
| 10,201,620 B2 | 2/2019 | Meis et al. | |
| 10,983,123 B2 | 4/2021 | Lakshmipathy et al. | |
| 2005/0042595 A1 | 2/2005 | Haas | |
| 2005/0054093 A1 | 3/2005 | Haas | |
| 2005/0059152 A1 | 3/2005 | Tanavde et al. | |
| 2005/0124003 A1 | 6/2005 | Atala et al. | |
| 2005/0148074 A1 | 7/2005 | Davies et al. | |
| 2007/0134210 A1 | 6/2007 | Heidaran | |
| 2007/0243172 A1 | 10/2007 | Ra et al. | |
| 2007/0298497 A1 | 12/2007 | Antwiler | |
| 2009/0191159 A1 | 7/2009 | Sakurada et al. | |
| 2010/0113327 A1 | 5/2010 | Van Leeuwen et al. | |
| 2010/0124569 A1 | 5/2010 | Abbot et al. | |
| 2010/0136679 A1 | 6/2010 | Min et al. | |
| 2010/0323446 A1 | 12/2010 | Barnett et al. | |
| 2011/0256110 A1 | 10/2011 | Perin et al. | |

(Continued)

FOREIGN PATENT DOCUMENTS

| AU | 2014201181 | 3/2014 |
|---|---|---|
| CN | 1407088 | 4/2003 |

(Continued)

OTHER PUBLICATIONS

Saguil et al., American Family Physician, 2012, vol. 85, No. 4, pp. 352-358 (Year: 2012).*
Flow Rate Units Conversion, Traditional Oven, 5 pages, retrieved from the internet (May 2022): https://www.traditionaloven.com/tutorials/flow-rate/convert-gtt-drop-per-minute-to-ml-milliliter-per-hour.html (Year: 2022).*
Li et al., Respiratory Research 2014, 15: 120, 14 pages (Year: 2014).*
Wilson et al., NIH Public Access (24 pages), published in final form as: Lancet Respir Med. Jan. 2015; 3(1): 24-32 (Year: 2015).*
Flow Rate Units Conversion, Traditional Oven, 5 pages, retrieved from the internet (May 2022): https://www.traditionaloven.com/tutorials/flow-rate/convert-gtt-drop-per-minute-to-ml-milliliter-per-hour.html (Year: 2022).*

(Continued)

*Primary Examiner* — Evelyn Y Pyla
(74) *Attorney, Agent, or Firm* — Knobbe, Martens, Olson & Bear, LLP

(57) ABSTRACT

Methods for purifying, culturing and selecting mesenchymal stem cell (MSC) subpopulations with neonatal quality and adult tissue specificity are for in production of advanced therapeutic medicinal products. In certain examples, term amniotic fluid derived cells having characteristics of lung cells can be isolated. In some the term amniotic fluid derived cells having characteristics of lung cells can be used in the treatment of acute and chronic respiratory diseases.

8 Claims, 17 Drawing Sheets

(56) References Cited

U.S. PATENT DOCUMENTS

| | | |
|---|---|---|
| 2012/0142102 A1 | 6/2012 | Chen et al. |
| 2012/0190731 A1 | 7/2012 | Messina |
| 2013/0157353 A1 | 6/2013 | Dijkhuizen Borgart et al. |
| 2013/0171110 A1 | 7/2013 | Woods et al. |
| 2014/0038291 A1 | 2/2014 | Ahlfors et al. |
| 2014/0369968 A1 | 12/2014 | Slukvin et al. |
| 2015/0247852 A1 | 9/2015 | Lakshmipathy et al. |
| 2016/0030489 A1 | 2/2016 | Larsson et al. |
| 2016/0068815 A1 | 3/2016 | Larsson et al. |
| 2016/0199413 A1* | 7/2016 | Simonson .............. A61K 35/16 435/325 |
| 2018/0059109 A1 | 3/2018 | Hsuan et al. |
| 2018/0119104 A1 | 5/2018 | Slukvin et al. |
| 2019/0064164 A1 | 2/2019 | Lakshmipathy et al. |
| 2020/0048609 A1 | 2/2020 | Saxena et al. |
| 2020/0056156 A1 | 2/2020 | Ino et al. |
| 2020/0095551 A1 | 3/2020 | Woods et al. |
| 2020/0171097 A1 | 6/2020 | Larsson et al. |

FOREIGN PATENT DOCUMENTS

| | | |
|---|---|---|
| CN | 202569006 | 12/2012 |
| CN | 202723948 | 2/2013 |
| CN | 109777773 A | 5/2019 |
| CN | 109971709 A | 7/2019 |
| DE | 202004012970 | 12/2005 |
| EP | 2302036 | 3/2011 |
| EP | 2479261 | 7/2012 |
| EP | 3029137 | 1/2019 |
| EP | 3117828 | 2/2020 |
| JP | 2005323534 | 11/2005 |
| JP | 2010529851 | 9/2010 |
| JP | 2010265220 | 11/2010 |
| JP | 2011084566 | 4/2011 |
| JP | 2012521780 | 9/2012 |
| JP | 2012255025 | 12/2012 |
| WO | WO 0235992 | 5/2002 |
| WO | WO 03042405 | 5/2003 |
| WO | WO 03068937 | 8/2003 |
| WO | WO 05078073 | 8/2005 |
| WO | WO 06012404 | 2/2006 |
| WO | WO 2008/060139 | 5/2008 |
| WO | WO 2009/031818 | 3/2009 |
| WO | WO 2009/052132 | 4/2009 |
| WO | WO 2009/135206 A1 | 11/2009 |
| WO | WO 10099539 | 9/2010 |
| WO | WO 2012/021845 | 2/2012 |
| WO | WO 2012/070032 | 5/2012 |
| WO | WO 2013/082487 | 6/2013 |
| WO | WO 2014/055121 | 4/2014 |
| WO | WO 2014/140913 | 9/2014 |
| WO | WO 2015/016761 | 2/2015 |
| WO | WO 2015/023720 | 2/2015 |
| WO | WO 2015/073786 | 5/2015 |
| WO | WO 2016/120310 | 8/2016 |
| WO | WO 2018/073615 | 4/2018 |
| WO | WO 2018/083700 | 5/2018 |
| WO | WO 2018/169554 | 9/2018 |
| WO | WO 2018/185584 | 10/2018 |
| WO | WO 2018/186421 | 10/2018 |
| WO | WO 2019/035880 | 2/2019 |
| WO | WO 2019/104381 A1 | 6/2019 |
| WO | WO 2021/087436 | 5/2021 |

OTHER PUBLICATIONS

Li et al., Respiratory Research 2014, 15: 120, 14 pages (Year: 2014).*
Wilson et al., NIH Public Access (24 pages), published in final form as: Lancet Respir Med. Jan. 2015; 3(1): 24-32 (Year: 2015).*
International Search Report from PCT/SE2020/050993 dated Apr. 15, 2021.
Allard et al., "Immunohistochemical Toolkit for Tracking and Quantifying Xenotransplanted Human Stem Cells." Regenerative Medicine 9.4 (2014): 437-452.
De Coppi, et al., "Isolation of Amniotic Stem Cell Lines with Potential for Therapy". Nature Biotechnology vol. 25, No. 1 (2007) 100-106.
Djouad, et al., "Mesenchymal Stem Cells: Innovative Therapeutic Tools for Rheumatic Diseases." Nature Reviews Rheumatology 5.7 (2009): 392-399.
Ge et al. "The Size of Mesenchymal Stem Cells is a Significant Cause of Vascular Obstructions and Stroke". Stem Cell Reviews and Reports, Apr. 10, 2014(2): 295-303.
Hoogduijn et al., "Morphology and Size of Stem Cells From Mouse and Whale: Observational Study." Bmj 347 (2013).
Kuroda et al. "Treatment of A Full-Thickness Articular Cartilage Defect in the Femoral Condyle of an Athlete with Autologous Bone-Marrow Stromal Cells." Osteoarthritis and Cartilage, vol. 15, No. 2 (2007): 226-231.
Pak, "Regeneration of Human Bones in Hip Osteonecrosis and Human Cartilage in Knee Osteoarthritis With Autologous Adipose-Tissue-Derived Stem Cells: A Case Series." J Med Case Reports 5. 296 (2011).
Vega, et al., 2017. "High-Content Image Informatics of The Structural Nuclear Protein Numa Parses Trajectories for Stem/Progenitor Cell Lineages and Oncogenic Transformation". Exp. Cell Res. 351:11-23.
International Search Report from PCT/SE2020/050994, dated Feb. 15, 2021 in 19 pages.
Bossolasco et al. "Molecular and phenotypic characterization of human amniotic fluid cells and their differentiation potential", Cell Research, 2006 16: pp. 329-336.
Hamid AA et al.,"Highly potent stem cells from full-term amniotic fluid: A realistic perspective" Reprod Biol, 2017, 17(1):9-18; whole document.
Han J et al., "Genetically modified mesenchymal stem cell therapy for acute respiratory distress syndrome", stem Cell Res Ther, 2019, 10(1 ):386; whole document.
Kim YW etal., "Time-course transcriptional profiling of human amniotic fluid-derived stem cells using microarray" Cancer Res Treat, 2010, 42(2):82-94; whole document.
Lee FY et al., "Xenogeneic human umbilical cord-derived mesenchymal stem cells reduce mortality in rats with acute respiratory distress syndrome compl icated by sepsis", Oncotarget, 2017, 8(28):45626-45642; whole document.
Lesage et al.,"The amniotic fluid as a source of mesenchymal stem cells with lung-specific characteristics", Wiley Prenatal Diagnosis 2017, pp. 1093-1099.
Leng z et al.,"Transplantation of ACE2-Mesenchymal stem Cells Improves the Outcome of Patients with COVID-19 Pneumonia", Aging Dis, Mar. 9, 2020, 11(2):216-228; whole document.
Moraghebi et al., "Term amniotic fluid: an unexploited reserve of mesenchymalstromal cells for reprogramming and potential cell therapy applications" Stem Cell Res Ther, 2017,8(1):190; whole document.
"Spitzhorn et al., ""Isolation and Molecular Characterization of Amniotic Fluid-Derived Mesenchymal Stem Cells Obtained from Caesarean Sections""", Hindawi Stem Cells International, vol. 2017, Article ID 5932705, in 15 pages."
Vadasz s et al ., "Second and third trimester amniotic fluid mesenchymal stem cells can repopulate a de-cellularized lung scaffold and express lung markers", J Pediatr Surg, 2014, 49(11 ):1554-63; whole document.
Zhou J et al., "Amniotic fluid-derived mesenchymal stem cells: characteristics and therapeutic applications" Arch Gynecol Obstet, 2014, 290(2):223-231; whole document.
Anker et al., "Isolation of Mesenchymal Stem Cells of Fetal or Maternal Origin from Human Placenta," Stem Cells, vol. 22, 2004, p. 1338-1345.
Bar-Nur et al., "Epigenetic Memory and Preferential Lineage-Specific Defferentation in Induced Pluripotent Stem Clles Derived from Human Pancreatic Isley Bets Cells", Cell Stem Cell vol. 9, No. 1, 2011, pp. 17-23.

(56) References Cited

OTHER PUBLICATIONS

Bieback et al., "Clinical Protocols foe the Isolation and Expansion of Mesenchymal Stromal Cells", Transfucion Medicine and Hemotherapy, 2008, vol. 35, pp. 286-294. (Year: 2008).
Bongso et al., "Taking Stem Cells to the Clinic: Major Challenges," Journal of Cellular Biochemisty, vol. 105, 2008, p. 1352-1360.
Bottai et al., "Third trimester amniotic fluid cells with the capacity to develop neural phenotypes and with heterogeneity among subpopulations," Restorative Neurology and Neuroscience, vol. 30, 2012, p. 55-68.
Cao et al., Stem Cell Repair of Central Nervous System Injury Neuroscience Res vol. 68, 2002, pp. 501-510.
Carette et al., "Generation of iPSCs from cultured human malignant cells", Blood, vol. 115, No. 20, 2010, pp. 4039-4042.
Chanda et al., "Retinoic Acid Signaling Is Essential for Embryonic Hematopoietic Stem Cell Development", Cell, vol. 155, No. 1, Sep. 26, 2013, pp. 215-227, XP028729738, ISSN: 0092-8674, DOI: 10.1016/J.CELL.2013.08.055.
Cipolleschi et al ("The Role of Hypoxia in the Maintenance of Hematopoietic Stem Cells," Blood, vol. 82, No. 7 (Oct. 1, 1993: pp. 2031-2037).
Dewar et al. "Imatinib inhibits the in vitro development of the monocyte/macrophage lineage from normal human bone marrow progenitors" Leukemia (2003) vol. 17 pp. 1713-1721.
de Wynter et al., "Comparison of Purity and Enrichment of CD34 + Cells from Bone marrow, Umbilical Cord and Peripheral Blood (primed for Apheresis) Using Five Separation Systems", Stem Cells, 1995, vol. 13, pp. 524-532.
Dobreva et al.,"On the origin of amniotic stem cells: of mice and men," The International Journal of Developmental Biology, vol. 54, 2010, p. 761-777.
Eggerman J et al.,"Endothelial progenitor cell culture and differentiation in vitro: a methodological comparison using human umbilical cord blood", Cardiovascular Research, Oxford University Press, GB, vol. 58, No. 2, May 1, 2003 (May 1, 2003), pp. 478-486, XP002351441, ISSN: 0008-6363, DOI: 10.1016/0008-6363(03)00252-9 002351441 I.
Forman et al., Reactive Oxygen Species and Cell Signaling, Respiratory Burst in Macrophage Signaling vol. 166 pp. 54-58, 2002.
Forraz et al., "The umbilical cord: a rich and ethical stem cell source to advance regenerative Medicine," Cell Proliferation, vol. 44, 2011, p. 60-69.
Friedman et al., "Umbilical Cord Mesenchymal Stem Cells: Adjuvants for Human Cell Transplantation," American Society for Blood and Marrow Transplantation, vol. 13, 2007, p. 1477-1486.
Goichberg et al., "CAMP-induced PKC activation increases functional CXCR4 expression on human CD34+ hematopoietic progenitors" Blood, vol. 107, No. 3, Feb. 1, 2006.
Ghosh et al., "Persistnat Donor Cell Gene Expression among Human Induced Pluripotent Stem Cells Contributes to Differences with Human Embryonic Stem Cells", Plos One, vol. 5, No. 2, 2010, p. E8975.
Halliwell, "Cell Culture, Oxidative Stress, and Antioxidants: Avoiding Pitfalls", Biomed J. vol. 37, No. 3, May-Jun. 2014.
Hanna et al.,"Direct cell reprogramming is a stochastic process amenable to acceleration"., Nature vol. 462, No. 7273, 2009, pp. 595-601.
Hong, D.K., et al., "Combined treatment with Dichloroacetic acid and pyruvate reduces hippocampal neuronal death after transient cerebral ischemia," Frontiers in Neurology, Mar. 2018, vol. 9, Article 137 (in 11 pages).
Iizuka, H., et al., "Targeted gene correction of RUNX1 in induced pluripotent stem cells derived from familial platelet disorder with propensity to myeloid malignancy restores normal megakaryopoiesis," Experimental Hematology, 2015, vol. 43, pp. 849-857.
Ikehata et al."Environmenatal Molecular Mutagenesis", vol. 41, No. 4, 2003, pp. 280-292.
Ikehata et al.,"Mutation spectrum in sunlight-exposed", vol. 556, No. 1-2, 2004, pp. 11-24.

Ingram D A et al.,"Identification of a novel hierarchy of endothelial progenitor cells using human peripheral and umbilical cord blood", Blood, American Society of Hematology, US, vol. 104, No. 9, Nov. 1, 2004 (Nov. 1, 2004), pp. 2752-2760, XP002351443, ISSN: 0006-4971, DOI: 10.1182/Blood-2004-04-1396 002351443 X.
Kim et al.,"Epigenetic memory in induced pluripotent stem cells", vol. 467, No. 7313, 2010, pp. 285-290.
Kettle et al ("Mechanism of inactivation of myeloperoxidase by 4-aminobenzoic acid hydrazide," Biochem. J. (1997) 321, 503-508).
Kinney, M.A., et al., "A systems biology pipeline identifies regulatory networks for stem cell engineering," Nature Biotechnology, 2019, vol. 37, pp. 810-818.
Kumano et al., "Generation of Induced pluripotent stem cells from primaty chronic myelogenous leukemia patient samples", Blood vol. 119, No. 26, 2012, pp. 6234-6242.
Lee et al., "Derivation of neural crest cells from human pluripotent stem cells". Nature protocols 5:88-701 (2010).
Lindencrona et al., "CD4+ T Cell-Mediated Her-2/Neu-Specific Tunor Rejection In The Absence of B Cells"., Int J Cancer vol. 109, 2004, pp. 259-264.
Lith et al. ("Engineering biodegradable polyester elastomers with antioxidant properties to attenuate oxidative stress in tissue," Biomaterials. Sep. 2014 ; 35(28): 8113-8122).
L. M. Reid, "Stem cell biology, hoemone/matrix synergies and liver differentiation". Current Opinion in Cell Biology, vol. 2, 1990, p. 121-130.
Ma, Q-S., et al., "Ligand-based design, synthesis and biological evaluation of xanthine derivatives as LSD1/KDM1A inhibitors," European Journal of Medicinal Chemistry, 2018, vol. 162, pp. 555-567 (Accepted Manuscript).
Marchetto et al., "Transcriptional Signature and Memory Retention of Human-Induced Pluripotent Stem Cells". Plos One vol. 4, No. 9, 2009, p. E7076.
Masip at al., "Reprogramming with defined factors: from induced pluripotency to induced transdifferentiation"., Molecular Human Reproduction, vol. 16, No. 11 pp. 856-868, 2010.
Melissa Ann Brown et al., "Umbilical Cord Blood Derived Endothelial Progenitor Cells: Isolation, Characterization, and Adhesion Potential in Vitro and in Vivo",, Jan. 1, 2009 (Jan. 1, 2009), XP055140385, Retrieved from the Internet: URL:http://hdl.handle.net/10161/1355 055140385 X.
Mareschi et al., "Multipotent Mesenchymal Stromal Stem Cell Expansion by Plating Whole Bone Marrow at a Low Cellular Density: A More Advantageous Method for Clinical Use", Stem Cells International, 2012, vol. 2012, pp. 1-10. (Year: 2010).
Maurice et al., "Isolation of progenitor cells from cord blood using adhesion matrices", Cytotechnology, 2007, vol. 54, pp. 121-133.
McGuckin et al., "Culture of embryonic-like stem cells from human umbilical cord blood and onward differentiation to neural cells in vitro," Nature Protocols, vol. 3, 2008, p. 1046-1055.
Mizuno et al., "Generation of skeletal muscle stem/progenitor cells from murine induced pluripotent stem cells," The Journal of the Federation of American Societies for Experimental Biology, vol. 24, 2010, p. 2245-2253.
Murphy et al., "Amnion Epithelial Cell Isolation and Characterization for Clinical Use," Current Protocols in Stem Cell Biology, vol. 13, 2010, p. 1-25.
M. V. Wiles, Embryonic Stem Cell Differentiation in vitro Meth. EnzymolL. vol. 225, 1993, p. 900.
Naik, P.O., et al., "Mitophagy-driven metabolic switch reprograms stem cell fate," Cellular and Molecular Life Sciences, Sep. 28, 2018, vol. 76, pp. 27-43.
Nijboer et al (Targeting the p53 Pathway to Protect the Neonatal Ischemic Brain, Ann Neural 2011; 70:255-264).
Oburoglu, L., et al., "Glucose and Glutamine Metabolism Regulate Human Hematopoietic Stem Cell Lineage Specification," Cell Stem Cell, 2014, vol. 15, pp. 169-184.
O'Donoghue et al., "Fetal stem cells," Best Practice & Research Clinical Obstetrics and Gynaecology, vol. 18, No. 6, pp. 853-875, 2004.
Osanai et al., "Enhanced expression of retinoic acid-metabolizing enzyme CYP26A1 in sunlight-damaged human skin"., vol. 44, No. 4, 2011, pp. 200-206.

(56) References Cited

OTHER PUBLICATIONS

Okabe et al., "Definitive proof for direct reprogramming of hematopoietic cells to pluripotency", Blood, 2009, vol. 114, No. 9, pp. 1764-1767.
Panopoulos et al.,"Rapid and Highly Efficient Generation of Induced Pluripotent Stem Cells from Human Umbilical Vein Endothelial Cells", PLOS One, vol. 6, No. 5, May 16, 2011 (May 16, 2011), p. e19743, XP055035699, DOI: 10.1371/journal.pone.0019743 055035699 X.
Park et al., "Disease-Specific Induced Pluripotent Stem Cells"., Cell vol. 134, No. 5, 2008, pp. 877-886.
Pereira et al., "Reproducible methodology for the isolation of mesenchymal stem cells from human umbilical cord and its potential for cardiomyocyte generation," Journal Of Tissue Engineering And Regenerative Medicine, vol. 2, 2008, p. 394-399.
Pelus, L.M., et al., "Peripheral Blood Stem Cell Mobilization: a Look Ahead," Current Stem Cell Reports, 2018, vol. 4, pp. 273-281.
Phuc et al., "Isolation of three important types of stem cells from the same samples of banked umbilical cord blood", Cell Tissue Bank, published online Jun. 8, 2011, vol. 13, pp. 341-351.
Polo et al.,"Cell type of origin influences the molecular and functional properties of mouse induced pluripotent stem cells"., Nature Biotechnology, vol. 28, No. 8, 2010, pp. 848-855.
P.D. Rathjen et al.,"Properies and uses of Embryonic Stem Cells Prospects for Application to Human Biology and Gene Therapy" Reprod. Fertil. Dev. vol. 10, 1998, p. 31.
Prigione et al. ("The Senescence-Related Mitochondrial/Oxidative Stress Pathway is Repressed in Human Induced Pluripotent Stem Cells," Stem Cells 2010:28:721-733).
Ronn et al., Reactive Oxygen Species Impair the Function of CD90+ Hematopoietic Progenitors Generated from Human Pluripotent Stem Cells. Sep. 1, 2016, vol. 35, No. 1; pp. 197-206; p. 2, 1st column, 2nd paragraph to 2nd column, 2nd paragraph; p. 3, 1st column, 1st and 2nd paragraphs; p. 4, 2nd column, 2nd paragraph; DOI: 10.1002/stem.2503.
Ronn et al., "Retinoic Acid Regulates Hematopoietic Development from Human Pluripotent Development from Human Pluripotent Stem Cells", Stem Cell Reports, vol. 4, No. 2, Feb. 1, 2015, pp. 269-281, XP055333217, United States ISSN: 2213-6711, DOI: 10.1016/j.stemcr.2015.01.009, p. 271, col. 1, paragraph 2.
Robertson,"Teratocarcinomas and embryonic stem cells: A practical approach", 1987, IRL Press Ltd.
Roubelakis, M.G., et al., "In vitro and in vivo properties of distinct populations of amniotic fluid mesenchymal progenitor cells," Journal of Cellular and Molecular Medicine, vol. 15, 2011, p. 1896-1913.
Salehinejad et al., "Comparison of different methods for the isolation of mesenchymal stem cells from human umbilical cord Wharton's jelly," In Vitro Cell.Dev.Biol.—Animal (2012) 48:75-83.
Saxena et al., "Cyclic AMP Signaling through Epac Axis Modulates Human Hemogenic Endothelium and Enhances Hematopoietic Cell Generation", Stem Cell Reports, vol. 6, No. 5, May 1, 2016, pp. 692-703, XP055333169, United States ISSN: 2213-6711, DOI: 10.1016/j.stemcr.2016.03.006 p. 695, col. 1, paragraph 2; figure 1.
Savickiene et al., "Human Amniotic Fluid Mesenchymal Stem Cells from Second- and Third-Trimester Amniocentesis: Differentiation Potential, Molecular Signature, and Proteome Analysis," Stem Cells International, 2015, in 15 pages.
Schiavo, A.A., et al., "Endothelial properties of third-trimester amniotic fluid stem cells cultured in hypoxia," Stem Cell Research & Therapy, (2015) 6:209, p. 1-15.
Seshareddy et al. "Method to Isolate Mesenchymal-Like Cells from Wharton's Jelly of Umbilical Cord," Methods in Cell Biology, vol. 86, 2008, p. 101-119.
Shigemura, T., et al., "Mosaicism of an ELANE mutation in an asymptomatic mother," Journal of Clinical immunology, Jan. 2019, vol. 39, pp. 106-111.
Suzuki, H., et al., "Glycolytic pathway affects differentiation of human monocytes to regulatory macrophages," Immunology Letters 176: 18-27 (2016), Accepted Manuscript.
Takahashi et al., "Induction of Pluripotent Stem Cells from Mouse Embryonic and Adult Fibroblast Cultures by Defined Factors"., Cell vol. 126, No. 4, 2006, pp. 663-676.
Uchida, N., et al., "Efficient generation of □-globin-expressing erythroid cells using stromal cell-derived induced pluripotent stem cells from patients with sickle cell disease," Stem Cells, 2017, vol. 33, pp. 586-596.
Vodyanik, M.A., et al., "Leukosialin (CD53) defines hematopoietic progenitors in human embryonic stem cell differentiation cultures," Blood, 2006, vol. 108, pp. 2095-2105.
Vizcardo et al. "Regeneration of Human Tumor Anitigen-Specific T Cells from iPSCs Devrived from Mature CD8 T Cells", Cell Stem Cell, Jan. 3, 2013, vol. 12, No. 1, pp. 31-36.
Wang et al ("Calpain inhibitor attenuates ER stress-induced apoptosis in injured spinal cord after bone mesenchymal stem cells X transplantation," Neurochemistry International 97: 15-25 (Jul. 2016).
Wassarman et al., "Guide to Techniques in Mouse Development", Methods in Enzymology vol. 225, 1993.
Weiss et al., "Stem Cells in the Umbilical Cord," Stem Cell Review, vol. 2, 2006, p. 155-162.
Wisniewski et al. (Further phenotypic characterization of the primitive lineage-CD34+CD38-CD90+CD45Ra-hematopoietic stem cell/ progenitor cell sub-population isolated from cord blood, mobilized peripheral blood and patients with chronic myelogenous leukemia. Blood Cancer Journal. 2011).
You, Q., et al., "Isolation of human mesenchymal stem cells from third-trimester amniotic fluid," International Journal of Gynecology and Obstetrics, vol. 103, 2008, p. 149-152.
Ye et al.,"Human-induced pluripotent stem cells from blood cells of healthy donors and patients with acquired blood disorders"., Blood vol. 114, No. 27, 2009, pp. 5473-5480.
Yu et al., "Induced Pluripotent Stem Cell Lines Derived from Human Somatic Cells"., Science vol. 318, No. 5858, 2007, pp. 1917-1920.
Zhou et al., "Generation of human induced pluripotent stem cells from urine samples," Nature Protocols, vol. 7, 2012, p. 2080-2089.
International Search Report and Written Opinion for PCT/US2017/023090 dated Aug. 15, 2017 in 16 pages.
International Search Report and Written Opinion for PCT/IB2016/001628 dated Jan. 24, 2017 in 14 pages.
International Search Report in PCT/SE2020/051139 dated Jan. 28, 2021.
International Preliminary Report on Patentability and Written Opinion for PCT/IB2016/001628 dated May 2, 2019 in 8 pages.
International Preliminary Report on Patentability and Written Opinion for PCT/US2017/023090 dated Sep. 26, 2019 in 7 pages.

\* cited by examiner

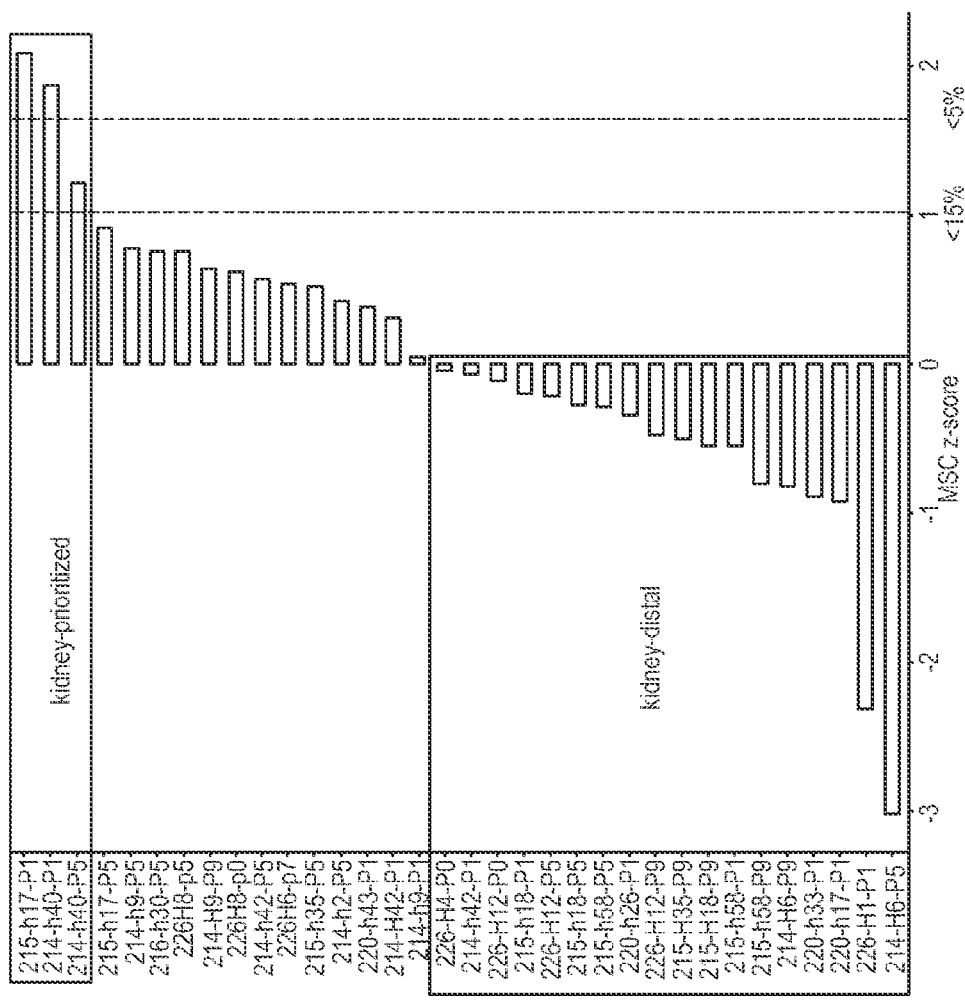

USE OF TERM AMNIOTIC FLUID CELLS FOR THE TREATMENT OF ACUTE AND CHRONIC RESPIRATORY DISEASES

FIELD OF THE INVENTION

The present invention relates to methods for purifying, culturing and selecting mesenchymal stem cell (MSC) subpopulations with neonatal and/or lung quality tissue specificity for use in production of advanced therapeutic medicinal products for the treatment of acute respiratory distress syndrome.

BACKGROUND OF THE INVENTION

The novel coronavirus disease 2019 (COVID-19) was first detected in Wuhan, China, from there expanding into a global pandemic affecting almost the entire world. COVID-19 is caused by the virus SARS-CoV-2, which attaches to the abundant cell surface protein ACE2, which is present in significant numbers on cells in the alveoli of the lung. COVID-19 has been shown to primarily affect the lungs, leading to both acute and chronic respiratory diseases, including Acute Respiratory Distress Syndrome (ARDS). ARDS is typically induced by either known or unknown environmental factors including viral (such as SARS-CoV-2, the virus that causes COVID-19) or bacterial infection that induces pulmonary tissue damage and inflammatory responses. As of yet, no drug or vaccine has been clearly shown to cure patients with COVID-19, therefore there is a need for new treatments. In particular, modulating and/or reducing the well-documented and potentially lethal "cytokine storm" inflammatory response in COVID-19 patients may improve patient health and survival.

Acute respiratory disorders may affect both children and adults and are particularly life threatening for elderly patients. There are also acute respiratory complications specific to premature neonates where damage from breathing in the underdeveloped lung develops into a chronic disease during childhood and adolescence. Additional respiratory disorders, such as chronic lung disorders, may be caused by long term exposure to environmental factors (pollution or smoke), such as idiopathic pulmonary fibrosis (IPF) and chronic obstructive pulmonary disease (COPD) typically affect the elderly. Further respiratory diseases of note include interstitial pneumonia and sepsis.

Mesenchymal Stromal cells and/or Mesenchymal Stem cells have been studied for their use in the treatment of numerous inflammatory diseases due to their immune modulatory effects and positive effects in tissue remodeling and regeneration. As such, both acute and chronic forms of respiratory diseases and disorders have been considered and tested for therapeutic effect using these cells. MSC medication should be an effective means to treat these respiratory disorders and diseases by promoting a modulated immune response in the damaged tissue allowing for tissue regeneration and stabilization. As explained by Zhao et al in their article "Transplantation of ACE2-Mesenchymal Stem Cells Improves the Outcome of Patients with COVID-19 Pneumonia," published in Aging and Disease March 2020, and incorporated by reference herein and attached as Appendix A, MSCs have been shown to be an effective treatment in patients with COVID-19 pneumonia. However, MSCs derived from additional cell sources, such as from amniotic fluid, and selected for particular lung markers, may provide further advantages for the treatment of both acute and chronic respiratory diseases, including ARDS.

The amniotic fluid is the liquid surrounding and protecting the fetus during pregnancy. During the last trimester, the amniotic fluid is partly secreted by the fetal lung and partly by fetal urine. The amniotic fluid is ingested orally and is absorbed by the gut of the fetus and thus re-enters the fetal circulation. Full term amniotic fluid consists of water with electrolytes, but also contains proteins, carbohydrates, lipids, phospholipids, and urea. In addition to these metabolic products, amniotic fluid also contains fetal cells and other materials chafed off the skin such as hair and vemix, a greasy deposit covering the skin of a baby at birth. Tissue interfaces in contact with the amniotic fluid contribute to content of the amniotic fluid including cellular material. The lung is the largest of those surfaces, which also secrete lung surfactant into the T.A.F. The oral and nasal mucosa, the eye, and the urinary tract are other such surfaces with a non-keratinized epithelial interface in topological contact with the amniotic fluid.

Mesenchymal stem cells (MSCs) can be found in nearly all tissues and are mostly located in perivascular niches. As will be understood by one of skill in the art, mesenchymal stem cells are multipotent stromal cells capable of differentiating into numerous cell types, and also possessing anti-inflammatory, angiogenic properties for directing tissue repair processes, thereby making mesenchymal stem cells valuable for therapeutic treatments. Term amniotic fluid (TAF) collected during a caesarean section contains a number of valuable cells, including MSCs. However, extracting and growing the MSCs has not previously been performed on a large scale due to difficulties associated with sterilely collecting, handling the TAF and identifying and extracting the MSCs. Moreover, specific subpopulations of MSCs are likely to be particularly well suited to use for production of therapeutic drugs. Previously, MSCs sourced from adult bone marrow, adult adipose tissue or neonatal birth-associated tissues including placenta, umbilical cord and cord blood were extensively used to obtain MSCs. MSCs from these neonatal tissues may have additional capacities in comparison to MSCs derived from adult sources. Indeed, several studies have reported superior biological properties such as improved proliferative capacity, life span and differentiation potential of MSCs from birth-associated tissues over adult derived MSCs. For example, the journal article "Term amniotic fluid: an unexploited reserve of mesenchymal stromal cells for reprogramming and potential cell therapy applications" by Woods et al. and published in *Stem Cell Research & Therapy* explains some of the advantages of birth-associated tissues over adult derived MSCs. However, neither of these neonatal MSC sources have a corresponding tissue or organ in the adult body. Therefore, neonatal quality MSCs with adult tissue specificity would be extremely beneficial. Moreover, acquisition of fetal material may be linked to negative consequences for the infant. For example, in cord blood harvesting it has been shown that as much of the cord blood as possible should be returned to the infant for improved survival, growth and fine motor skills development. Amniotic fluid, on the other hand, is today considered medical waste that is discarded. Therefore, both the ethical and practical incentive to harvest such an untapped resource is clear. Consequently, there is a need for new methods and materials that utilize TAF-derived cells in the treatment of various respiratory disease states, such as COVID-19 induced ARDS.

SUMMARY OF THE INVENTION

Certain disclosed examples relate to devices, cells, methods, and systems for obtaining amniotic mesenchymal stem cells from amniotic fluid and cells derived thereof. It will be understood by one of skill in the art that application of the devices, methods, and systems described herein are not limited to a particular cell or tissue type. Further examples are described below.

In some examples, a method of treating acute respiratory distress syndrome in a patient in need thereof may comprise:
  administering term amniotic fluid (TAF) lung mesenchymal stem cells (MSCs) to the patient, wherein the Lung TAF MSCs have been obtained by:
    performing adherence selection on TAF cells to obtain TAF adherence cells;
    passaging the TAF adherence cells to obtain TAF mesenchymal stem cells (TAF MSCs); and
    selecting TAF MSCs to obtain lung TAF MSCs.

In certain examples, selecting TAF MSCs to obtain Lung TAF MSCs may comprise selecting TAF MSCs that express Endosialin. Selecting TAF MSCs to obtain Lung TAF MSCs may comprise selecting TAF MSCs that express DDR1. Selecting TAF MSCs to obtain Lung TAF MSCs may comprise selecting TAF MSCs that express LRRC38. Selecting TAF MSCs to obtain lung TAF MSCs may comprise selecting TAF MSCs that express a Group A surface marker selected from the group consisting of PCDH19, DDR1, MME, IFITM10, BGN, NOTCH3, SULF1, TNFSF18, BDKRB1, FLT1, PDGFRA, TNFSF4, UNC5B, FAP, CASP1, CD248, DDR2, PCDH18, LRRC38, and CRLFL Selecting may further comprise a first sorting step to direct TAF MSCs that express Endosialin into a first output group, wherein the selecting TAF MSCs that express the Group A surface marker may be a second sorting step to direct TAF MSCs from the first output group into a second output group. In certain examples, selecting lung TAF MSCs may comprise excluding TAF MSCs that express a Group B surface marker selected from the group consisting of CD24, ITGB4, TNFSF10, GFRA1, CD74, FGFR4, HAVCR1, and OSCAR. The lung TAF MSCs may be administered at a concentration of about 1-2 million cells per kg. Administering the lung TAF MSCs may comprise administering the lung TAF MSCs via an intravenous drip. The intravenous drip may comprise about 40 drops per minute.

In certain examples, a method for obtaining lung mesenchymal stem cells from amniotic fluid may comprise:
  providing term amniotic fluid (TAF);
  removing particulate material from the TAF to obtain purified TAF cells;
  performing adherence selection on the purified TAF cells to obtain TAF adherence cells;
  passaging the TAF adherence cells to obtain TAF mesenchymal stem cells (TAF MSCs); and
  selecting TAF MSCs that express Endosialin to obtain Lung TAF MSCs.

In certain examples, the step of selecting TAF MSCs that express Endosialin to obtain lung TAF MSCs may further comprise selecting lung TAF MSCs that express a Group A surface marker selected from the group consisting of PCDH19, DDR1, MME, IFITM10, BGN, NOTCH3, SULF1, TNFSF18, BDKRB1, FLT1, PDGFRA, TNFSF4, UNC5B, FAP, CASP1, CD248, DDR2, PCDH18, LRRC38, and CRLF1. The step of selecting TAF MSCs that express Endosialin to obtain lung TAF MSCs may further comprise excluding TAF MSCs that express a Group B surface marker selected from the group consisting of CD24, ITGB4, TNFSF10, GFRA1, CD74, FGFR4, HAVCR1, and OSCAR. The selecting step may comprise selecting TAF MSCs that express at least two surface markers from the Group A surface markers. The selecting step may comprise selecting TAF MSCs that express at least three surface markers from the Group A surface markers. The selecting step may comprise selecting TAF MSCs that express at least four surface markers from the Group A surface markers. Isolated cells obtainable by the methods described above may express Endosialin.

In some examples, a population of term amniotic fluid (TAF) lung mesenchymal stem cells (MSCs) for use in a method of treating acute respiratory distress syndrome in a patient in need thereof, may be obtained by:
  performing adherence selection on TAF cells to obtain TAF adherence cells;
  passaging the TAF adherence cells to obtain TAF mesenchymal stem cells (TAF MSCs); and
  selecting TAF MSCs to obtain Lung TAF MSCs.

In certain examples, a composition may comprise the isolated population of term amniotic fluid (TAF) mesenchymal stem cells described above and a pharmaceutically acceptable carrier for said TAF mesenchymal stem cells.

In certain aspects, the disclosure provides methods and apparatuses for isolating lung term amniotic fluid (TAF) mesenchymal stem cells and treatments involving same according to one or more features of the foregoing description and/or figures.

BRIEF DESCRIPTION OF THE DRAWINGS

FIG. 16 is an example graph showing tissue-prioritized and tissue-distal data using kidney tissue as an example, including tissue-prioritized data greater than 15% percentile.

DETAILED DESCRIPTION OF THE PREFERRED EXAMPLES

Figure 1:
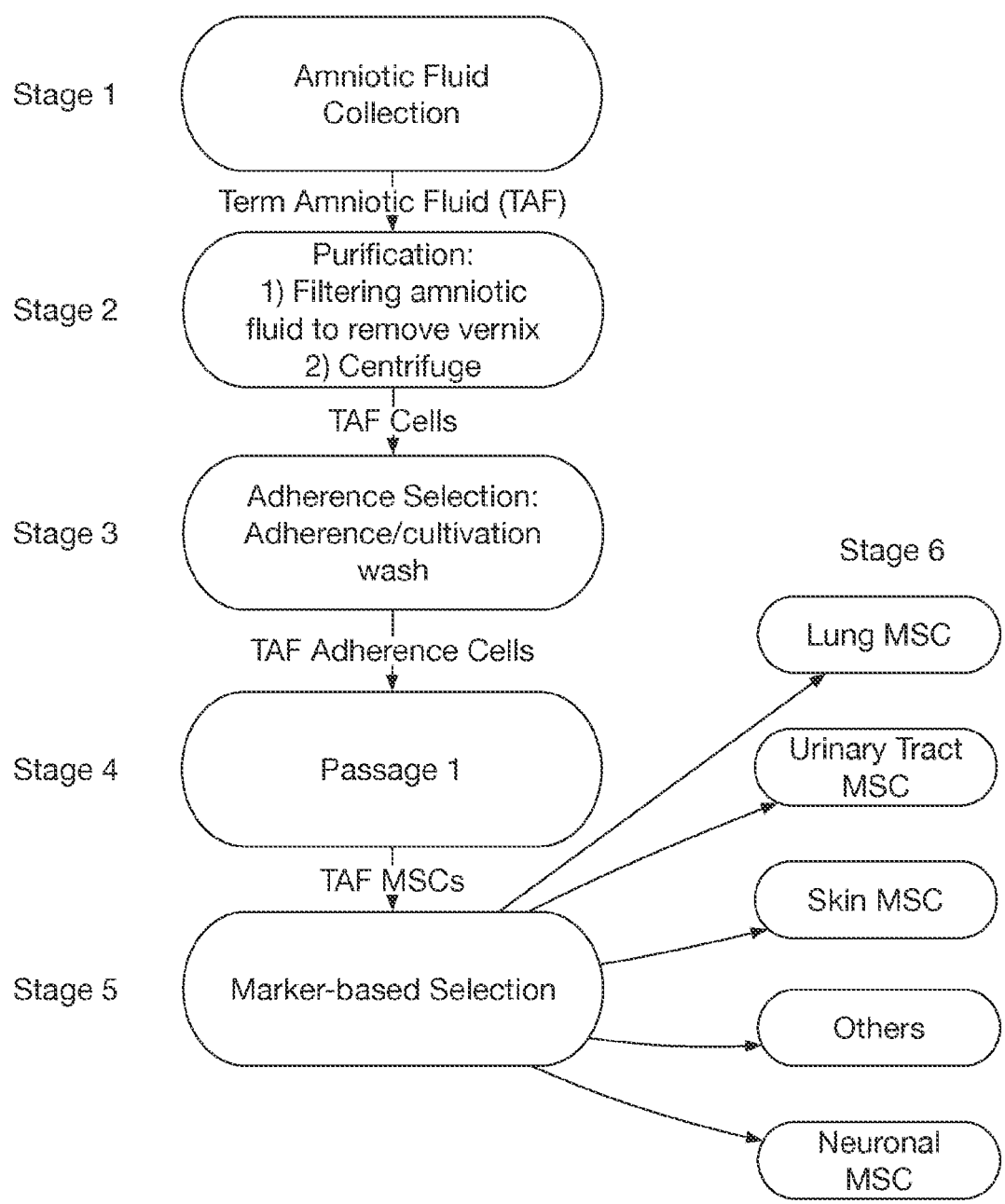
FIG. 1 is a flow diagram showing the steps in the purification, culturing and selection of MSC subpopulations.

Methods of purifying, culturing and selecting MSC subpopulations with neonatal quality and adult tissue specificity are summarized in FIG. 1 and described in detail below. Examples disclosed herein relate to apparatuses and methods for collecting, purifying, isolating, expanding, differentiating, and maturing amniotic fluid-derived cells. The examples disclosed herein are not limited to collection of a certain type of amniotic-derived cell and the technologies disclosed herein are broadly applicable to different cells and tissues.

Amniotic Fluid Collection

Figure 2:
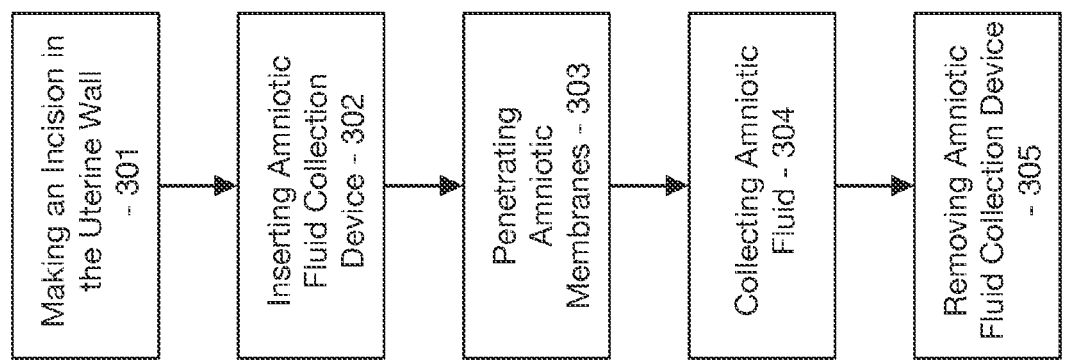
FIG. 2 is a diagram illustrating a method for collecting amniotic fluid.

Amniotic fluid may be collected to produce term amniotic fluid (TAF) according to the methods described in U.S. patent application Ser. No. 14/776,499 (corresponding to US2016/0030489), the entire content of which is incorporated by reference. Specifically, FIG. 2 is a block diagram of an example of a method 300 of amniotic fluid collection, according to an exemplary example of the invention. It should be appreciated that method 300 may include any number of additional or alternative tasks. The tasks shown in FIG. 3 need not be performed in the illustrated order, and method 300 may be incorporated into a more comprehensive procedure or process having additional functionality not described in detail herein.

As shown in FIG. 2, method 300 may include making an incision in the uterine wall 301 of a pregnant mother, for example, during caesarean section. Step 301 may be performed with a standard physician's scalpel. As also shown in FIG. 2, method 300 may include inserting an amniotic fluid collector 302 through the incision in the uterine wall made in Step 301. Method 300 also includes penetrating the amniotic membrane 303 using the amniotic fluid collector of Step 302. Step 303 may also include penetrating the chorionic membrane. In one aspect, the tip is inserted to a 10 cm depth. In some examples, the tip is inserted to a depth of about 3 cm to about 30 cm. In some examples, the tip is inserted to a depth of about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, or about 29 cm.

Method 300 further includes collecting the amniotic fluid 304 from the amniotic sac using the amniotic fluid collector of Step 302. Step 304 may include initiating a siphon to transfer the amniotic fluid to a collection chamber of the amniotic fluid collector, such as by opening an inlet valve of the amniotic fluid collector. Step 304 may also include positioning a collection chamber of the amniotic fluid collector below an inlet of the amniotic fluid collector. Step 304 may also include coupling a negative pressure source to an outlet of the amniotic fluid collector to initiate transfer of the amniotic fluid. Step 304 may include relocating an inlet of the amniotic fluid collector to retrieve substantially all of the available amniotic fluid.

Finally, method 300 includes removing the amniotic fluid collector 905 from the amniotic sac. Step 905 may include closing an inlet valve of the amniotic fluid collector. In one example, no blood is visible in the collected material. Step 905 may also include emptying the collection system for further use/processing and sterilizing the exterior of the entire device. In one example, the exterior is sterilized using 70% ethanol so that the sterility may be maintained in any post-processing steps, such as in a laminar air flow bench setup, e.g., for isolation of cell material according to the present invention, and for fluid storage.

In one example, the amniotic fluid collection procedure is performed in less than one minute. In one example, the amniotic fluid collection procedure is performed in one to two minutes. In one example, the amniotic fluid collection procedure is performed in not more than three minutes. In one example, the method is simplified compared to standard operating procedures for cesarean sections, for example, by preventing spillage of the amniotic fluid into the operating wound, improving visibility and physical access. In one example, fetal skin is unaffected by the device tip.

Purification

Amniotic Fluid Collection

Amniotic fluid may be collected to produce term amniotic fluid (TAF) according to the methods described in U.S. patent application Ser. No. 14/776,499 (corresponding to US2016/0030489), the entire content of which is incorporated by reference. Specifically, FIG. 2 is a block diagram of an example of a method 300 of amniotic fluid collection, according to an exemplary example of the invention. It should be appreciated that method 300 may include any number of additional or alternative tasks. The tasks shown in FIG. 3 need not be performed in the illustrated order, and method 300 may be incorporated into a more comprehensive procedure or process having additional functionality not described in detail herein.

As shown in FIG. 2, method 300 may include making an incision in the uterine wall 301 of a pregnant mother, for example, during caesarean section. Step 301 may be performed with a standard physician's scalpel. As also shown in FIG. 2, method 300 may include inserting an amniotic fluid collector 302 through the incision in the uterine wall made in Step 301. Method 300 also includes penetrating the amniotic membrane 303 using the amniotic fluid collector of Step 302. Step 303 may also include penetrating the chorionic membrane. In one aspect, the tip is inserted to a 10 cm depth. In some examples, the tip is inserted to a depth of about 3 cm to about 30 cm. In some examples, the tip is inserted to a depth of about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 2 1 cm, about 22 cm, about 23 cm, about 24 cm, about 25 cm, about 26 cm, about 27 cm, about 28 cm, or about 29 cm.

Method 300 further includes collecting the amniotic fluid 304 from the amniotic sac using the amniotic fluid collector of Step 302. Step 304 may include initiating a siphon to transfer the amniotic fluid to a collection chamber of the amniotic fluid collector, such as by opening an inlet valve of the amniotic fluid collector. Step 304 may also include positioning a collection chamber of the amniotic fluid collector below an inlet of the amniotic fluid collector. Step 304 may also include coupling a negative pressure source to an outlet of the amniotic fluid collector to initiate transfer of the amniotic fluid. Step 304 may include relocating an inlet of the amniotic fluid collector to retrieve substantially all of the available amniotic fluid.

Finally, method 300 includes removing the amniotic fluid collector 905 from the amniotic sac. Step 905 may include closing an inlet valve of the amniotic fluid collector. In one example, no blood is visible in the collected material. Step 905 may also include emptying the collection system for further use/processing and sterilizing the exterior of the entire device. In one example, the exterior is sterilized using 70% ethanol so that the sterility may be maintained in any post-processing steps, such as in a laminar air flow bench setup, e.g., for isolation of cell material according to the present invention, and for fluid storage.

In one example, the amniotic fluid collection procedure is performed in less than one minute. In one example, the amniotic fluid collection procedure is performed in one to two minutes. In one example, the amniotic fluid collection procedure is performed in not more than three minutes. In one example, the method is simplified compared to standard operating procedures for cesarean sections, for example, by preventing spillage of the amniotic fluid into the operating wound, improving visibility and physical access. In one example, fetal skin is unaffected by the device tip.

Purification

Term amniotic fluid (TAF) is purified by filtering term amniotic fluid to remove vernix. Although the term 'term amniotic fluid' is employed here and elsewhere in the present disclosure, it is understood that methods, processes, and devices of the present disclosure may be applied to all amniotic fluids and not just term amniotic fluid. Term amniotic fluid may be amniotic fluid collected at term caesarean section deliveries using, for example, a closed catheter-based system. For the purposes of the present description, 'term amniotic fluid' may be amniotic fluid collected at planned cesarean sections after 37 completed weeks of pregnancy or later, or at planned cesarean section close to term, for example after 36 completed weeks of pregnancy. Preferably, term amniotic fluid is taken at planned caesarean sections during week 37 of pregnancy or later.

Figure 3:
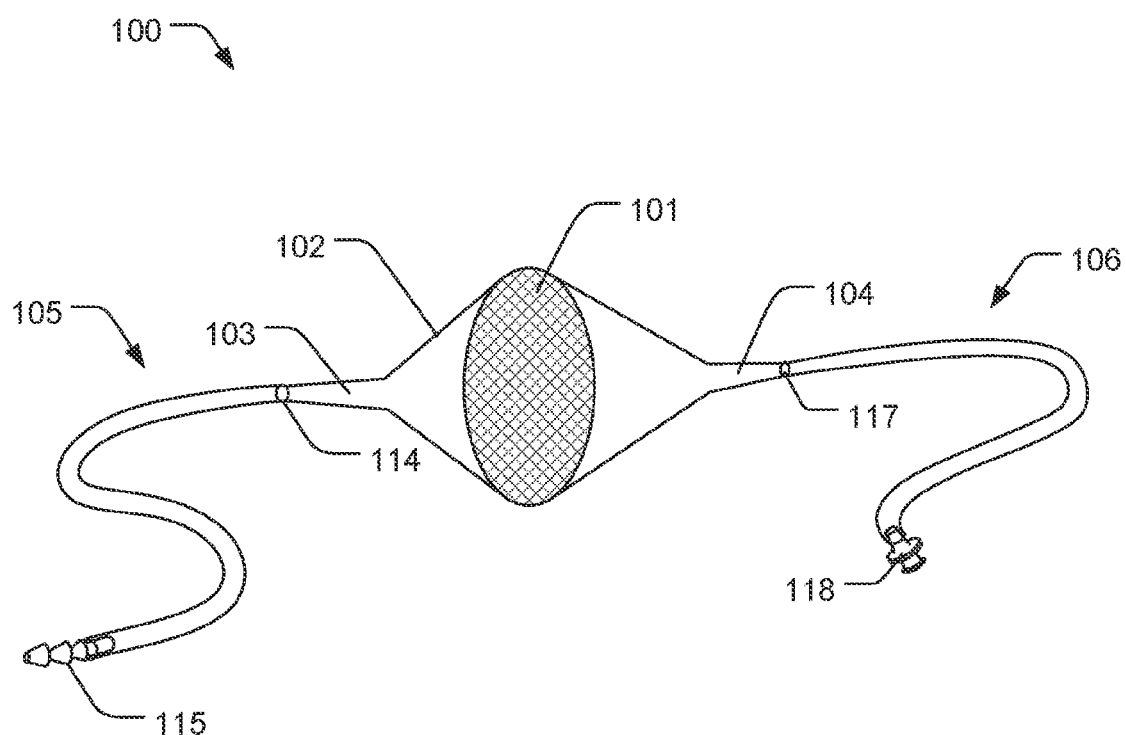
FIG. 3 is a schematic illustration, in a perspective view, of an apparatus for filtering amniotic fluid according to an example.
Figure 4:
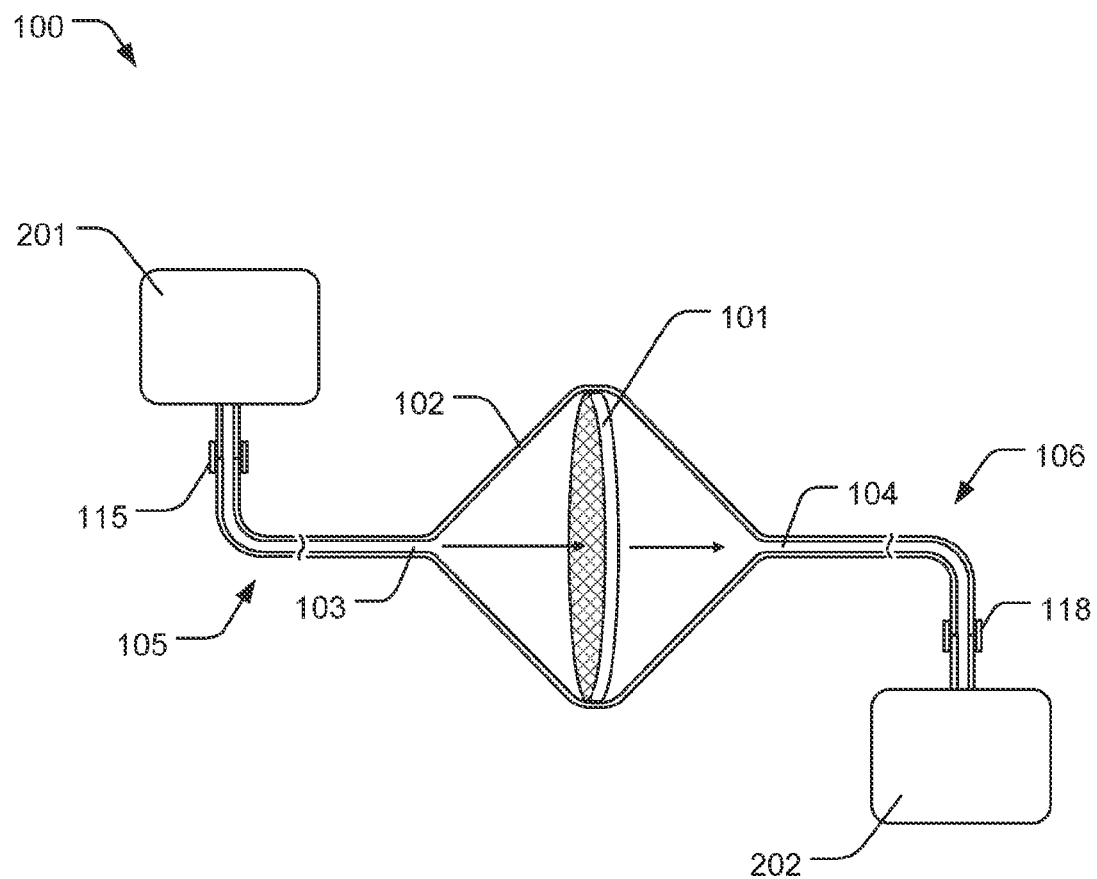
FIG. 4 is a schematic illustration, in a cross-sectional side view, of an apparatus for filtering amniotic fluid according to an example.
Figure 12:
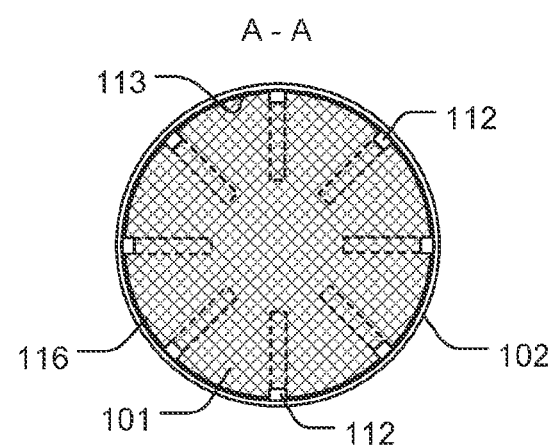
FIG. 12 is a schematic illustration, in a cross-sectional side view, of an apparatus for filtering amniotic fluid according to an example.

FIG. 3 is a schematic illustration of an apparatus 100 for filtering amniotic fluid according to one example. The amniotic fluid contains amniotic cells originating from the fetus or the amniotic sac such as Mesenchymal stem cells. The amniotic fluid also contains other materials chafed off the skin such as hair and vernix. Material other than the amniotic cells are here referred to as particulate matter and may also comprise meconium, blood clots, etc. Particulate matter may be considered as anything larger than 20 pm. For the purposes of filtering, it may be particularly advantageous to treat anything larger than 30 pm or even 50 pm as particulate matter. Optionally, anything larger than the targeted amniotic cells may be treated as particulate matter. The amniotic fluid thus generally contains a mixture of amniotic cells and particulate matter. The apparatus 100 comprises a filter 101 for filtering the particulate matter from the amniotic fluid, and a chamber 102 enclosing the filter 101. The chamber 102 comprises a fluid inlet 103 and a fluid outlet 104. The chamber 102 enclosing the filter 101 should be construed as the filter 101 being isolated by the chamber towards the environment surrounding the chamber 102 such that there is no fluid communication between the amniotic fluid in the chamber 102 with said environment. Fluid communication through the chamber 102 is thus controlled via the fluid inlet 103 and the fluid outlet 104 in the example of FIG. 3. The filter 101 is attached to the inside of the chamber 102 between the fluid inlet 103 and the fluid outlet 104. FIG. 12 shows an example of a cross-section A-A as indicated in FIG. 12 of a circular chamber 102 and filter 101. It should however be understood that the chamber 102 and filter 101 may have varying shapes for optimization to different applications. The apparatus 100 comprises an inlet connector 105 arranged to form a sealing connection between the fluid inlet 103 and an amniotic fluid sample source 201 (shown in FIG. 4). FIG. 4 shows a schematic example of such source 201 of amniotic fluid. Having an inlet connector 105 connected to the fluid inlet 103 and configured to provide a sealing connection between the fluid inlet 103 directly to a source 201 of amniotic fluid provides for minimizing exposure to contaminants and an efficient aseptic handling of the amniotic fluid. This facilitates obtaining amniotic cells which allows post-filtration processing at an improved quality standard. Hence, an aseptic pharmaceutical production process is facilitated. The preparation of e.g. surfactant molecules may be facilitated. The apparatus 100 provides for improving the functioning of the amniotic stem cells, such as an improved engraftment phase following transplantation. Such improved processes are enabled by having the filter 101 enclosed in a chamber 102 and an inlet connector 105 arranged to form a sealing connection between the fluid inlet 103 of the chamber 102 and an amniotic fluid sample source 201. The risk of exposing the amniotic stem cells to contaminants, such as bacteria and viruses, is thus reduced. Exposure to oxygen is also minimized, which provides for reducing formation of oxygen free radicals which may negatively impact the functioning of the stem cells.

FIG. 3 shows an example where the inlet connector 105 comprises a tube 105 connected to the fluid inlet 103 at a first sealing connection 114. The inlet connector 105 may form a sealing connection with the fluid inlet 103 with a force-fitting connection, an adhesive, a clamp, or other fixation elements. In another example, such as schematically shown in FIG. 4, the inlet connector 105 is a continuous extension of the fluid inlet 103, without a separate fixation element, e.g. by being formed as a single piece by molding or other material forming techniques. FIGS. 3 and 4 show a second connector 115 configured to form a sealing connection with a sample source 201, such as a container or bag 201 containing amniotic fluid. The second connector 115 may comprise releasable force-fitting connection, a clamp, or a combination thereof, or other releasable fixation elements. The chamber 102, filter 101, fluid inlet 103, fluid outlet 104, and inlet connector 105 may be provided as a kit in a sterile packaging, e.g. as a disposable kit. Such kit, i.e. apparatus 100, thus provides for a facilitated and improved process of filtering and obtaining amniotic stem cells. Hence, in use, the amniotic fluid passes the filter 101 when flowing from the fluid inlet 103 to the fluid outlet 104. The particulate matter is thus deposited on the filter 101 and the amniotic fluid containing the amniotic cells flows through the fluid outlet 104. As seen in the example in FIG. 12, the filter 101 may be connected around its periphery 116 to the inner wall 113 of the chamber 102. This avoids passing of amniotic fluid from the inlet 103 to the outlet 104 without being filtered. The filter 101 may be tensioned or otherwise supported so that a folding or curving of the filter 101 in the chamber 102 is avoided, This maintains a defined mesh or pore size across the area of the filter 101 and thus defined filtering characteristics. Maintaining a defined mesh or pore size also reduces the risk of clogging the filter 101. Long-term performance may accordingly be improved.

The apparatus 100 may comprise an outlet 5 connector 106 to form a sealing connection between the outlet and an amniotic cell-receiving device 202, such as a centrifuge or other amniotic cell-processing equipment downstream of the apparatus 100. FIG. 4 shows a schematic example of such device 202. This minimizes exposure to contaminants and allows efficient aseptic handling of the amniotic fluid in post-filtering processing steps. FIG. 3 shows an example where the outlet connector 106 comprises a tube 106 connected to the fluid outlet 104 at a first sealing connection 117. The outlet connector 106 may form a sealing connection with the fluid outlet 104 with a force-fitting connection, an adhesive, a clamp, or other fixation elements. In another example, such as schematically shown in FIG. 4, the outlet connector 106 is a continuous extension of the fluid outlet 104, without a separate fixation element, e.g. by being formed as a single piece by molding or other material forming techniques. FIGS. 3 and 4 show a second connector 118 configured to form a sealing connection with an amniotic cell processing device downstream of the apparatus 100, such as a centrifuge 202. The second connector 118 may comprise a force-fitting connection, a clamp, a combination thereof, or other releasable fixation elements. The connection between the second connector 118 and e.g. a centrifuge 202 may thus be repeatedly connected and disconnected, and also re-sealable to maintain a sealing connection in such procedure. The chamber 102, filter 101, fluid inlet 103, fluid outlet 104, inlet connector 105, and outlet connector 106 may be provided as a kit in a sterile packaging, e.g. as a disposable kit. Such kit, i.e. apparatus 100, thus provides a facilitated and improved process of filtering and processing of amniotic stem cells. The apparatus 100 may comprise a pump 122, 123, arranged to pressurize the amniotic fluid to flow from the fluid inlet 103 to the fluid outlet 104. This provides for a more effective filtering of the amniotic fluid. Larger volumes may be filtered in less time.

Figure 6:
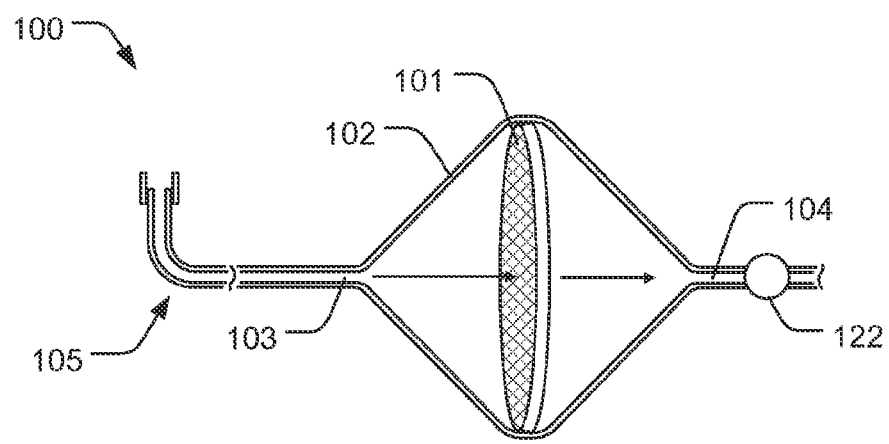
FIG. 6 is a schematic illustration, in a cross-sectional side view, of an apparatus for filtering amniotic fluid according to an example.

FIG. 6 shows an example where a pump 122 is connected to the fluid outlet 104 to draw amniotic fluid through the filter 101 in the direction of the indicated arrows. The pump 122 may be arranged at the fluid inlet 103 to push the amniotic fluid through the filter 101. The pump 122 may be a compact manually operated pump integrated with the fluid inlet 103, fluid outlet 104, inlet connector 105, or outlet connector 106.

Figure 7:
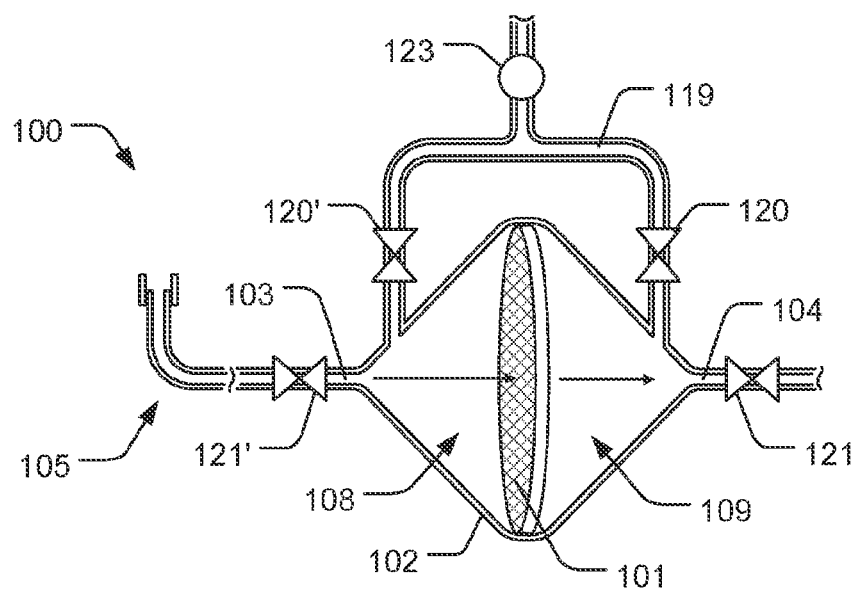
FIG. 7 is a schematic illustration, in a cross-sectional side view, of an apparatus for filtering amniotic fluid according to an example.

FIG. 7 shows another example, described in more detail below, where a pump 123 is arranged to pressurize the amniotic fluid to flow from the fluid inlet 103 to the fluid outlet 104. The chamber 102 may comprise a conduit 119 arranged between the fluid inlet 103 and the fluid outlet 104. The pressure in the chamber 102 may be variable in response to fluid and/or gaseous communication through the conduit 119. The flow of amniotic fluid through the filter 101 may thus be optimized depending on the application, e.g. the flow rate through the fdter 101 may be increased or decreased by varying the pressure in the chamber 102 via conduit 119.

Figure 5:
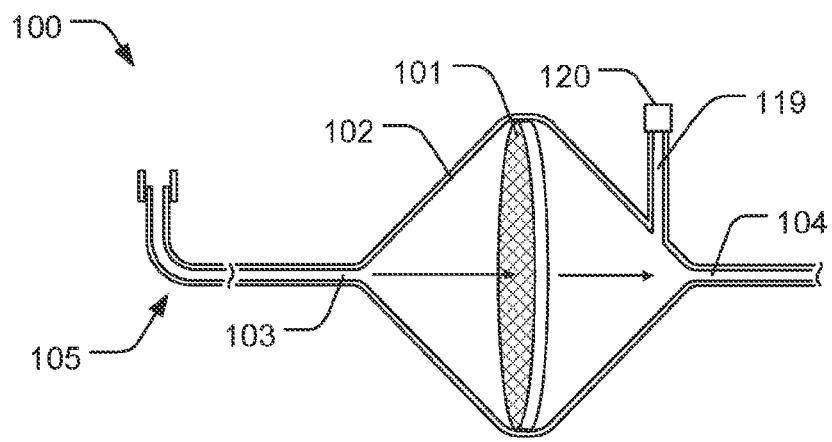
FIG. 5 is a schematic illustration, in a cross-sectional side view, of an apparatus for filtering amniotic fluid according to an example.

FIG. 5 shows an example in which a conduit 119 is in communication with the chamber 102. An access port 120, such as a connector or valve element, may be actuated to allow a fluid or gas to be expelled from the chamber 102, and/or injected into the chamber 102, to affect the pressure therein. The conduit 119 is arranged between the fluid outlet 103 and the fdter 101 in FIG. 5, but the conduit 119 may be arranged between the fluid inlet 103 and the fdter 101 in another example. FIG. 5 as described below shows a further example of a conduit 119 in communication with the chamber 102. A pump 123 may be arranged in communication with the conduit 119, as exemplified in FIG. 7. This facilitates optimization of the flow in the chamber 102 and the associated filtering process. In the example of FIG. 7 the conduit 119 is in variable communication with an upstream cavity 108 of the chamber 102 and a downstream cavity 109 of the chamber 102, i.e. the fdter 101 may be arranged to divide the chamber 102 into an upstream cavity 108 and a downstream cavity 109. In FIG. 7 the conduit 119 is connected to both the upstream cavity 108 and the downstream cavity 109. The pump 123 is arranged to pressurize the amniotic fluid to flow from the upstream cavity 108 to the downstream cavity 109, or to flow from the downstream cavity 109 to the upstream cavity 108. The latter case may be advantageous in a situation in which a momentary reversed flow is desired, e.g. to clear out clogging or occlusion of the filter 101. In such case, valves 120, 120', 121, 121', as schematically indicated in FIG. 7 are operated to provide the desired flow directions. E.g. for a reversed flow, valves 120 and 121' may be open and valves 120' and 121 may be closed. Valves 121, 121', may be open and\ valves 120, 120', may be closed in a normal filtering made. The upstream cavity 108 may be pressurized by also opening valve 120' in such filtering mode.

Figure 8:
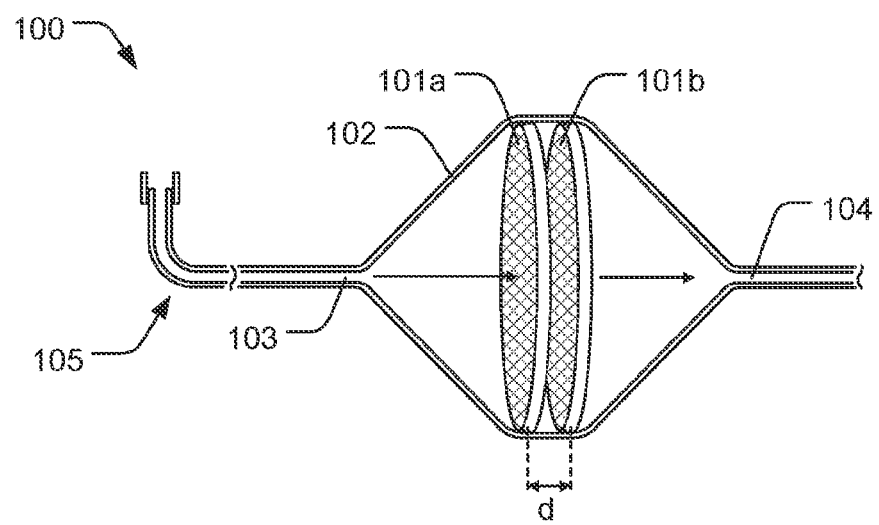
FIG. 8 is a schematic illustration, in a cross-sectional side view, of an apparatus for filtering amniotic fluid according to an example.

The filter 101 may comprise a first filter element 101a and a second filter element 101b arranged between the first filter element 101a and the fluid outlet 104, as schematically shown in FIG. 8. The second filter element 101b may have a mesh or pore size which is smaller than. a mesh or pore size of the first filter element 101a. This allows effective filtering of particulate matter of gradually smaller dimensions. The risk of filter occlusion is thus reduced. This allows for a more reliable and robust filtering process of the amniotic fluid. An improved filtering of amniotic fluid containing a greater range in the size of particulate matter is also provided. Further, a larger fraction of the stem cells in the amniotic fluid may be obtained since the stem cells are not lost in clogged pores. Although FIG. 8 two filter elements 101a, 101b, it should be understood that any plurality of filter elements may be arranged in sequence in the chamber 102, with gradually decreasing mesh or pore size, in the direction of fluid flow from the fluid inlet 103 to the fluid outlet 104, for an effective filtering of particulate matter of gradually decreasing dimensions. The first and second filter elements 101a, 101b, may be separated by a distance (d) along a direction amniotic fluid flaw from the fluid inlet 103 to the fluid outlet 104, as schematically indicted in the example of FIG. 8. The motion of the amniotic fluid between the first and second filter elements 101a, 101b, which in some case may involve turbid flow, may provide for further reducing the risk of unwanted build-up of particles on the first and second filter elements 101a, 101b.

The filter 101 may comprise a mesh having a mesh size in the range of 20-2000 pm. In another example, the filter 101 comprises a mesh having a mesh size in the range of 100-500 pm. This allows particularly effective filtration of particulate matter from the amniotic fluid. Turning again to FIG. 8, the first filter element 101a may comprise a mesh having a mesh size in the range of 500-1000 pm, and the second filter element 101b may comprise a mesh having a mesh size in the range of 30-150 pm. The first filter element 101a may thus remove larger debris, followed by removal of smaller particles with the second filter element 101b. This allows a particularly effective filtering of particulate matter of varying size and reliable filtering of increased volumes over longer time periods since the risk of clogging is further minimized. As previously mentioned, any plurality of filter elements may be arranged in succession in the chamber 102.

Figure 9:
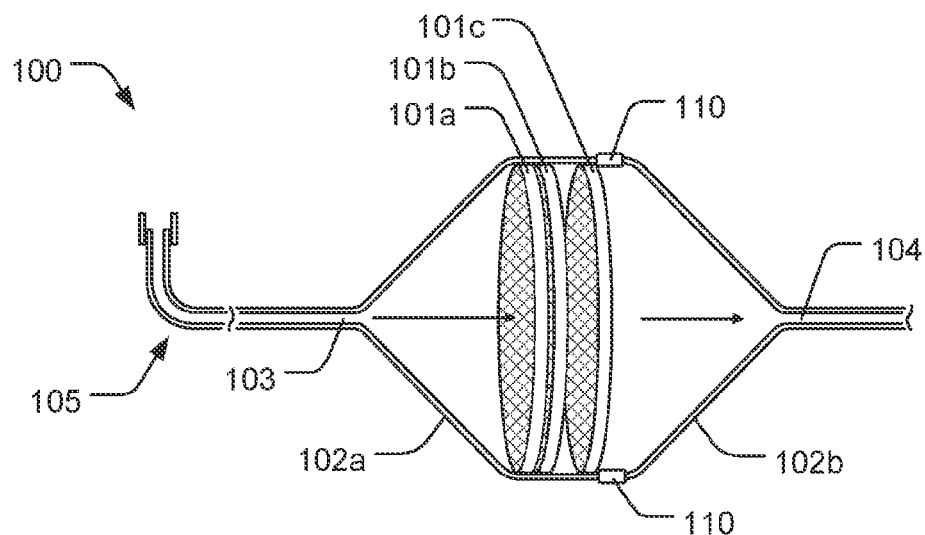
FIG. 9 a schematic illustration, in a cross-sectional side view, of an apparatus for filtering amniotic fluid according to an example.

FIG. 9 shows three filter elements 101a, 101b, 101c, arranged in the chamber 102. In some examples the filter element having the smallest mesh or pore size, arranged furthest downstream in the chamber 102 may, such as filter element 101b in FIG. 6 and filter element 101c in FIG. 9, may have a mesh or pore size dimensioned so that only single amniotic cells or amniotic cell clumps smaller than 10 cells pass through the filter 101. The smallest mesh or pore size in such an example may be approximately 30 pm. The filter 101 may comprise a mesh such as a nylon mesh. The filter 101 may comprise a porous material having a variable pore size through the filter 101 in the direction of flow of the amniotic fluid from the fluid inlet 103 to the fluid outlet 104. I.e. larger debris is removed at the surface of the filter 101 closest to the inlet 103 whereas particles of smaller size are removed deeper into the filter, as the amniotic fluid flows through the filter 101 in a direction towards the outlet 104 and the size of the pores get smaller. As previously mentioned, the chamber 102 may comprise an upstream cavity 108 and a downstream cavity 109. The upstream and downstream cavities 108, 109, may be formed as an integrated piece to form the chamber 102, e.g. in a molding process or by other material forming techniques. The upstream and downstream cavities 108, 109, may be formed as separate units which are then connected to each other to form a sealing connection, e.g. by an adhesive or by welding. The filter 101 may be attached simultaneously or subsequently with such welding process or by the aforementioned adhesive.

The upstream and downstream cavities 108, 109, may be releasably connectable to each other at a connecting element 110, to form a sealing connection, as schematically shown in FIG. 9. This allows opening of the chamber 102, e.g. for replacing the filter 101. The filter 101 may thus be releasably connectable to the chamber 102, e.g. filter elements 101a, 101b, 101c, may be releasably connectable to the chamber 102 in FIG. 7. This allows facilitated customization to different applications since filter elements 101a, 101b, 101c, of different pore or mesh size, or different number of such filter elements may be mounted in the chamber 102.

Figure 10:
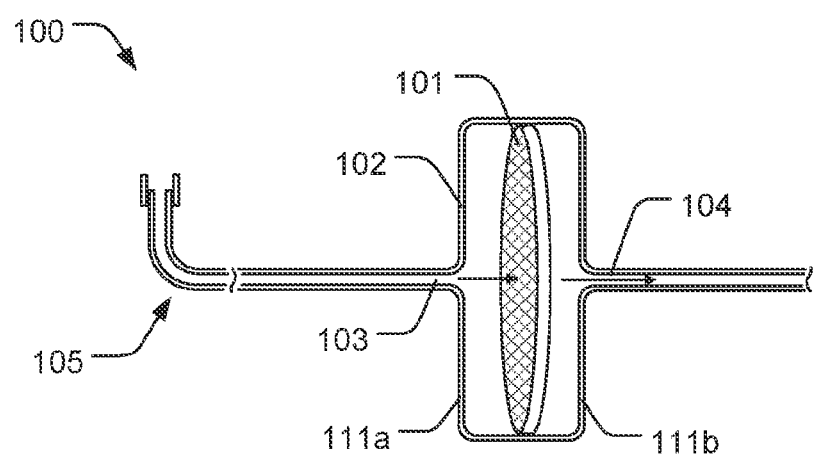
FIG. 10 is a schematic illustration, in a cross-sectional side view, of an apparatus for filtering amniotic fluid according to an example.
Figure 11:
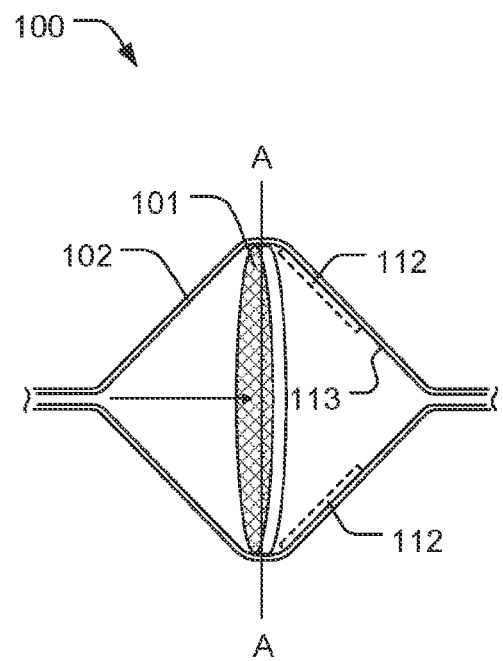
FIG. 11 is a schematic illustration, in a cross-sectional side view, of an apparatus for filtering amniotic fluid according to an example.

The connecting element 110 is configured to form a sealing connection upstream and downstream cavities 108, 109, and may comprise an annular gasket extending around the periphery of the upstream and downstream cavities 108, 109. The filter 101 may comprise a cartridge of different numbers of filter elements 101a, 101b, 101c, with different pore sizes that could be tailored to the particular amniotic fluid sample. For example, evaluation of the amniotic fluid turbidity and degree of milkiness (level of vernix both in particle size and opaqueness) could be an indicator of the appropriate filter cartridge to use. An accompanying chart for which to compare the amniotic fluid sample with could indicate which filter cartridge to use. The upstream cavity 108 and/or the downstream cavity 109 may be funnel shaped. FIGS. 3-9 show examples where both the upstream and downstream cavities 108, 109, are funnel shaped. FIG. 11 shows an example where only the downstream cavity 109 is funnel shaped. Having a funnel shape may be advantageous for directing the flow of amniotic fluid along a desired vector of symmetry through the filter 101 and apparatus 100. The upstream cavity 108 and/or the downstream cavity 109 may comprise a chamber wall 111a, 111b being arranged essentially in parallel with the filter 101, i.e. perpendicular to the direction of flow of the amniotic fluid from the fluid inlet 103 to the fluid outlet 104. FIG. 10 shows an example where chamber walls 111a, 111b, of the upstream and downstream cavities 108, 109 are arranged essentially in parallel with the filter 101. This minimizes the space inside the chamber 102, while maintaining adequate filter area, to minimize the risk of introducing e.g. air that may disturb surfactant molecules, reduce the risk of infection, and reduce detrimental formation of reactive oxygen species in the amniotic cells. The chamber 102, and/or the inlet connector 105, and/or the outlet connector 106 may be formed from a phthalate free PVC material. This provides for an apparatus which is suitable to be in contact with pharmaceutical starting materials such as amniotic cells.

The apparatus 100 may comprise protrusions 112 arranged to extend from an inner wall 113 of the chamber 102. FIGS. 11 and 12 show examples of such protrusions 112, in a cross-sectional side view and through cross-section A-A respectively. The protrusions 112 provides support for the fdter 101 in case the fdter 101 would start bend and fold towards the inner wall 113. Thus, a flow through the mesh or pores of the fdter 101 is still possible in such case since the fdter 101 may be supported by the protrusions 112 at a distance from the inner wall 113, i.e. the protrusions 112 allows for further limiting the risk of flow restriction and provides for an efficient, robust: and reliable filtering.

Figure 13:
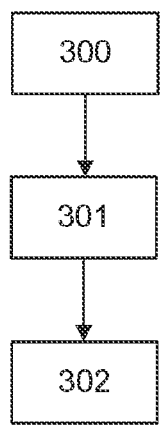
FIG. 13 is a flow chart of a method of filtering amniotic fluid according to an example.

FIG. 13 is a flow chart of a method 300 of filtering amniotic fluid containing particulate matter and amniotic cells. The method 300 comprises forming 301 a sealing connection between a fluid inlet 103 of a chamber 102 and an amniotic fluid sample source 201. The method 300 comprises passing 302 the amniotic fluid through a fdter 101 enclosed in the chamber 102 by providing a flow of the amniotic fluid from the fluid inlet 103 to a fluid outlet 104 of the chamber 102. Particulate matter is thereby deposited on the fdter 101 and the amniotic fluid containing amniotic cells flows through the outlet 104. The method 300 thus provides for the advantageous benefds as described in relation to apparatus 100 and FIGS. 3-12 above. The method 300 provides for effective and sterile filtration of the amniotic fluid to obtain amniotic cell samples of high quality.

In one embodiment, removing particulate material from the TAF to obtain purified TAF cells may be done by applying any known method in the art such as filtration, centrifugation, etc. The TAF may be filtered through a fdter having a pore size at or above 20 pm. The fdter may be made from any synthetic material including but not limited to cellulose acetate, cellulose nitrate (collodion), polyamide (nylon), polycarbonate, polypropylene and polytetrafluoroethylene (Teflon). In one embodiment removing particulate material is done by applying apparatus 100.

Adherence Selection

Various terms known to one skilled in the art have been and will be used throughout the specification, for example, the terms "express, expression, and/or expressing" in the context of a cell surface marker are meant to indicate the presence of a particular marker on the surface of a cell, said surface marker having been produced by the cell. Surface marker expression may be used to select between different cell populations, for example, positively selecting for surface marker expression indicates the selection of a cell population that more strongly expresses a particular surface marker as compared to another cell population. Conversely, negatively selecting for cell surface marker expression indicates the selection of a cell population that more weakly expresses a particular surface marker as compared to another cell population.

As explained above and elsewhere in the specifications, TAF contains various progenitor cell types. In certain examples, particular progenitor cell types may be isolated and propagated via adherence selection. For example, a vitronectin substrate, Synthemax (Merck, CORNING®, Synthemax®, II-SC SUBSTRATE, CLS3535-1EA) may be used as a coating to create a more in v/vo-like environment for stem cell culture, thereby limiting maturation of the TAF-derived progenitor cells and maintaining plasticity. Synthemax is an animal-component free, synthetic, flexible vitronectin-based peptide substrate for serum or serum-free expansion of human progenitor/stem cells and other adult stem cell types. One of skill in the art will understand that the vitronectin-based peptide substrate may include a portion of a vitronectin protein, such as a particular peptide sequence of vitronectin. Alternatively, intact vitronectin protein may be used. Synthemax vitronectin substrate offers a synthetic, xeno-free alternative to biological coatings and/or feeder cell layers commonly used in cell culture and known in the art. Briefly, standard tissue-culture treated flasks may be coated with about 0.2 mL Synthemax/$cm^2$ at 10 μg/mL giving a surface density of 2 $pg/cm^2$, and incubated at 37° C. for about 1 h, 5 h 2 h, 4 h, 8 h, or more than 8 h or at room temperature for about 2 h, 1 h, 4 h, 8 h or more than 8 h with surplus solution optionally being removed and replaced. In certain examples, Synthemax may be coated at a surface density of about: 1 to 5 $pg/cm^2$, such as 2 $pg/cm^2$, 0.1 to 10 $pg/cm^2$, 0.5 to 4 $pg/cm^2$, 1 to 3 $pg/cm^2$, or about 1.5 to 2.5 $pg/cm^2$.

In other embodiments, adherence selection can be performed using a surface coated with, for example, Collagen, Fibronectin. Alternatively, adherence selection can be performed using an uncoated surface comprising a tissue-culture treated plastic.

Cells purified from TAF fluid may be gently re-suspended in prewarmed xeno-free cell culture media, with the cell suspension is then added to the Synthemax-coated flasks. Media may be changed at various times after addition to the flasks, for example, after about: 2 h to 168 h, 12 h to 96 h, 24 h to 72 h, 36 h to 60 h, 42 h to 56 h, or 48 h, and then subsequently changed about: every day, every other day, every third day, every fifth day, once a week, once every two weeks or about less than once every two weeks. Through repeated removal of spent medium, the non-attached cells may be removed, thereby selecting the MSCs by their affinity for attachment to the Synthemax-treated surface. The cells may be cultured for a period of time, such as about, for example, 4 d, 7 d, 10d, 11d, 12 d, 13 d, 14 d, 18 d, 21 d, 28 d or longer than 21 d. Optionally, in some examples, the cells may be cultured under hypoxic conditions, hypoxia priming may alter cell metabolism during expansion, increase resistance to oxidative stress, and thereby improve the engraftment, survival in ischemic microenvironments, and angiogenic potential of transplanted MSCs. After culturing, the P0 colonies (Colony forming Units—CFUs) that have formed may be dissociated and pooled. After pooling, the remaining cells may be predominantly non-tissue specific MSCs. In certain examples, the pooled P0 cells may be gently re-suspended in pre-warmed xeno-free cell culture media and re-plated on tissue-culture treated flasks without Synthemax for passaging. The pooled cells may be seeded at a seeding density of from between about: 100 to 10000 $cells/cm^2$, 500 to 8000 $cells/cm^2$, 1000 to 5000 $cells/cm^2$, or about 2000 to 4000 $cells/cm^2$. The media may be changed about every 1d, 2 d, 4 d, or more than four days. After a period of time, such as about 2 d, 4 d, 7 d, or more than 7 d, the cells may be dissociated and harvested. Further selective MSC isolation may be achieved as described below.

Identification of Markers

When comparing the genetic expression profiles of TAF-MSCs and adult-type MSCs derived from adipose tissue or bone marrow by RNAseq, TAF-MSCs tend to express more of some genes present in adult-type MSCs and less of others. Identification of both positive and negative TAF-MSC specific neonatal cell-surface markers can allow for sorting of the MSCs with neonatal quality from those that have differentiated further and are of less importance as progenitor cells using e.g. ligands such as antibodies and aptamers or other selection techniques.

Figure 14:
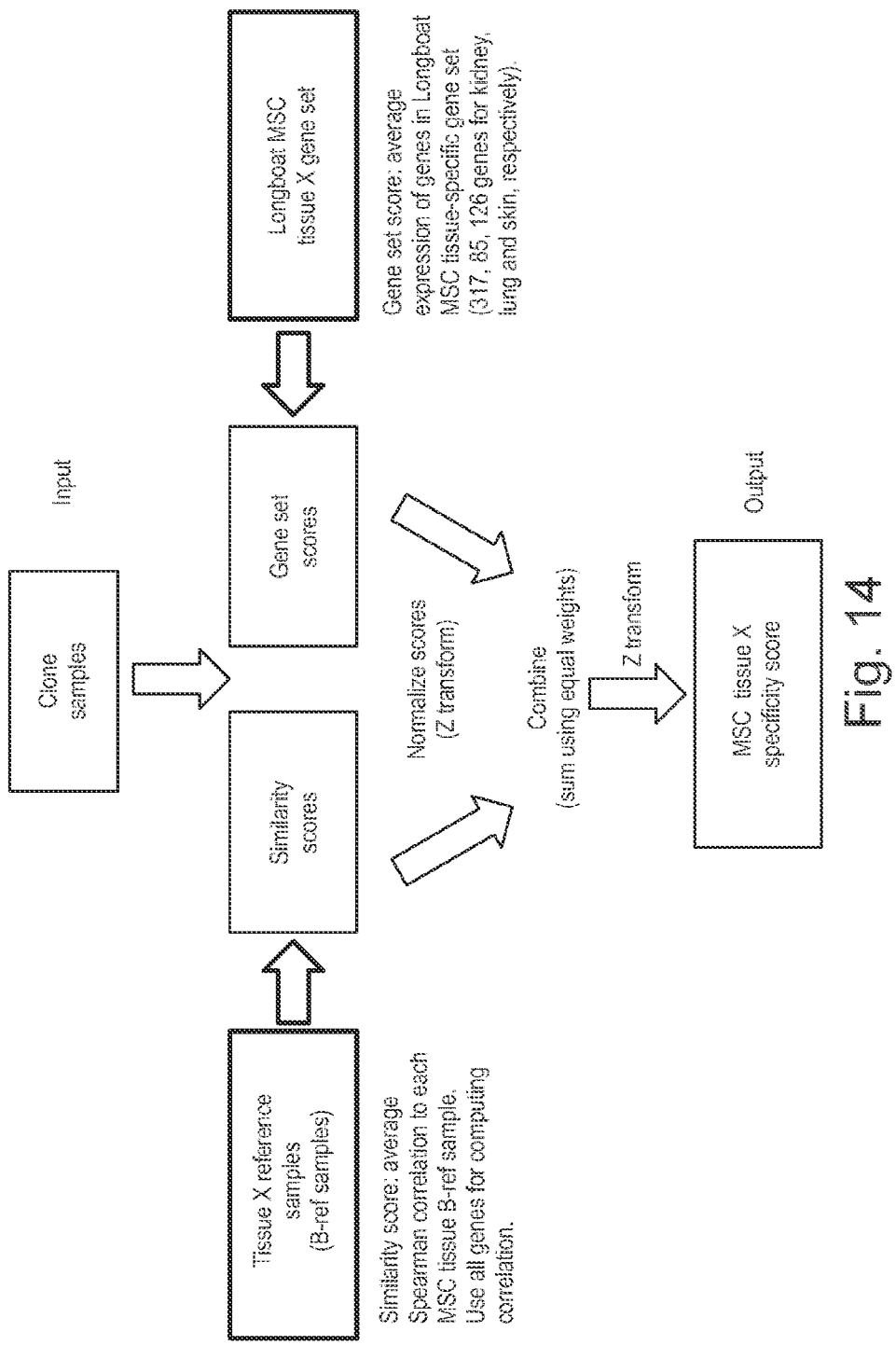
FIG. 14 is a flow chart showing the steps for calculation of an MSC tissue specificity score according to an example.

The cell surface markers distinguishing tissue relevant cells from other MSCs may be elucidated via a bioinformatics process utilizing a tissue-specificity score algorithm. An example of an MSC tissue-specificity score algorithm is shown in FIG. 14. Tissue-specificity may be measured as a combination of two components: a 'tissue transcriptional similarity' also known as a similarity score and a "tissue-specific gene expression program" also known as a gene set score. In certain examples, the similarity score may be an Average Spearman correlation to each MSC tissue reference sample (for example a fetal lung MSC sample). In examples, the gene set score may be the average expression of genes in a tissue-specific gene set. As shown in FIG. 14, in certain examples, after normalizing the similarity and gene set scores using a Z-transform to convert the input values, which is a sequence of real or complex numbers, into a complex frequency-domain representation, then combining them assigning equal weight to each score and transforming combined values using a Z-transform, the resulting output is an MSC tissue specificity score. The MSC tissue-specificity score measures the relative tissue-specificity among the input samples by measuring how many standard deviations a sample is more or less specific to a given tissue compared to the average input sample. For example, an MSC tissue-specificity score may indicate how much more a clone sample appears to have a tissue specific phenotype, such as a lung phenotype, as compared to an average clone. Such an approach allows for identification of the top X % percentile scores using a normal distribution function, effectively the top X % of clones that are most tissue-specific to the relevant tissue.

Figure 15:
FIG. 15 is an example graph showing MSC tissue specificity scores representing the 5% and 15% thresholds for various tissues.
Figure 17A:
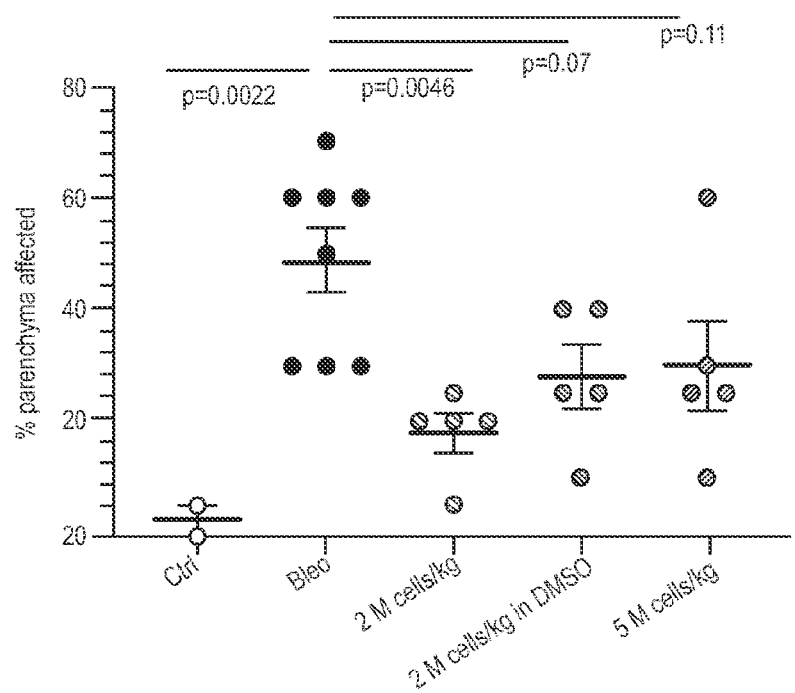
FIGS. 17A-17D show the results of an example study demonstrating the effects of using TAF Lung MSCs to treat rats with induced lung fibrosis.
Figure 17B:
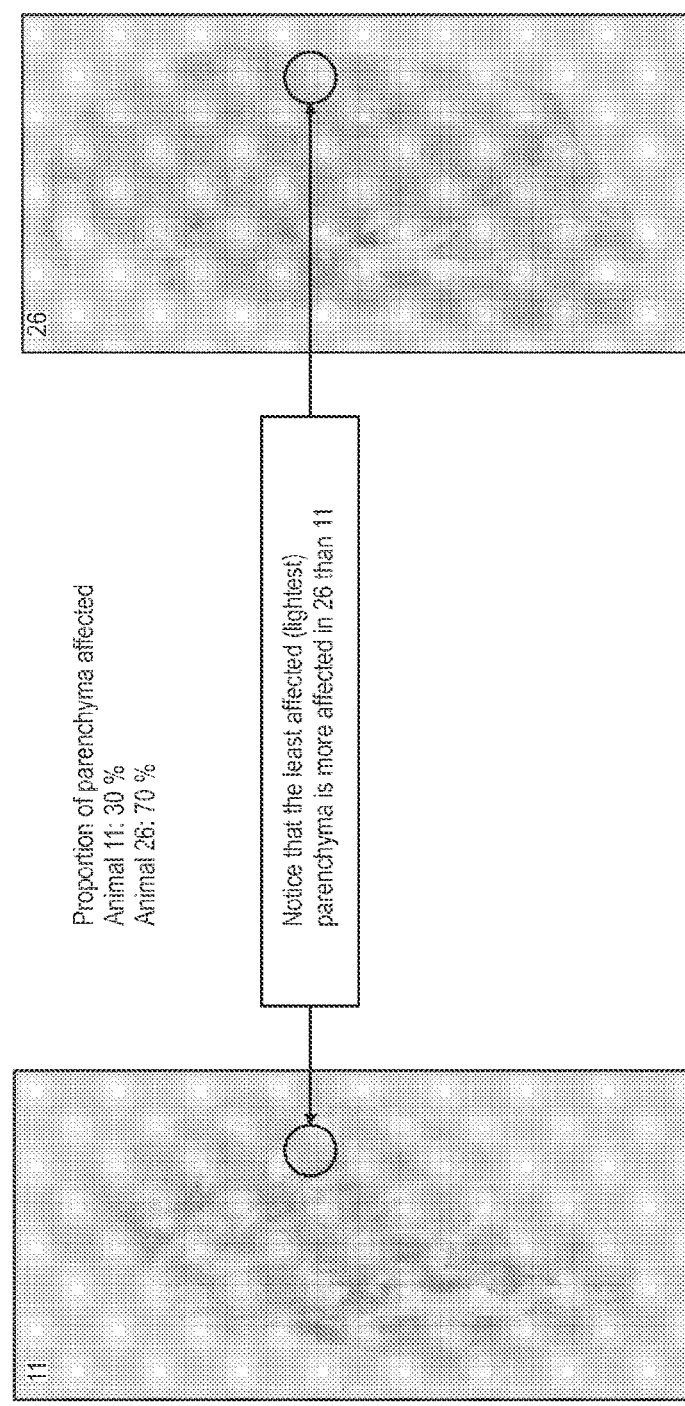
Figure 17C:
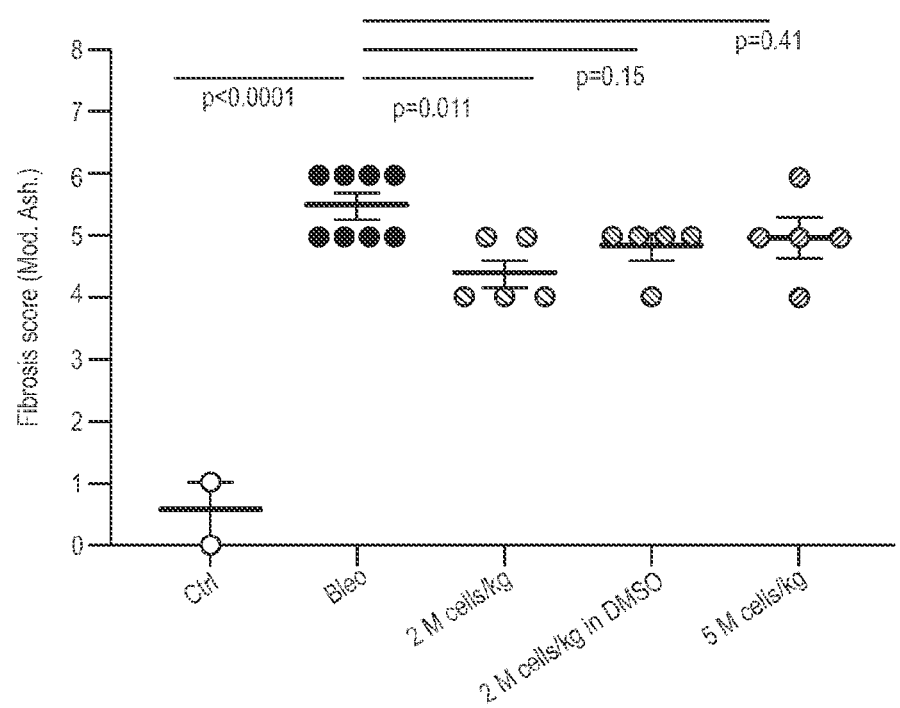
Figure 17D:
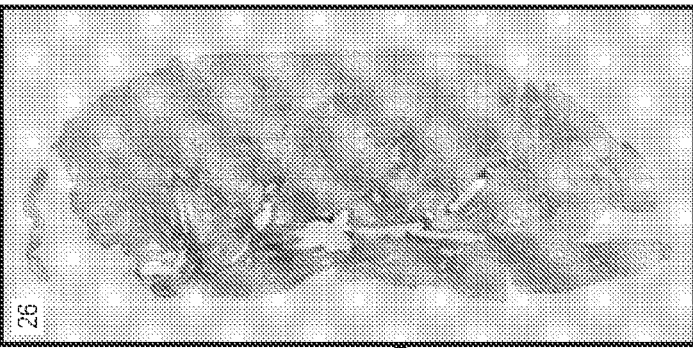

In one example, for a given tissue, tissue-prioritized clones can be defined as any clone belonging to the top X % percentile score, where X is any percentage within a range having a lower end from about 0.1 to 25, such as about 1, 5, 10, 15 and 20, and an upper end from about 30 to 75, such as about: 35, 40, 45, 50, 55, 60, 65 or 70. An example of TAF-MSC tissue-specificity prioritization results is shown in FIG. 15, in which thresholds at 15% and 5% are visible. Having prioritized tissue-specific clones, candidate surface marker genes may then be identified. For each tissue, two groups may be defined: tissue-prioritized and tissue-distal. A suitable analysis program may be used to make this determination, for example DEseq2 from Bioconductor.org. The tissue-prioritized group may include clones with a score in the top 15% percentile. The tissue-distal group may include clones in the bottom Y % percentile in which Y is any percentage within the range having a lower end from about 25 to 70, such as about: 30, 35, 40, 45, 50, 55, 60 or 65 and an upper end from 75 to 99.9, such as about: 80, 85, 90, 95 or 99. FIG. 16 shows an example of such analysis on kidney tissue. Next, differentially expressed genes between the tissue-prioritized and tissue-distal groups may be identified. Finally, the differential expression results may be annotated with surface marker gene information.

In certain examples, to identify tissue-specific cell surface markers, surface marker genes with a more than a Z-fold increase, where Z is at least about: 1.5-fold, 2-fold, 2.5-fold, 3-fold, 3.5-fold, 4-fold, 5-fold, 8-fold, 10-fold, 12-fold, 15-fold or even more-fold increase in expression (log2FoldChange) in prioritized clones compared to an average clone and a Transcripts Per Kilobase Million (TPM) of more than about 500, such as more than about: 1000, 1500, 2000, 2500, 3000, 5000 or even higher may be selected to give the top tissue-specific marker candidates, such as approximately the top: 5, 10, 20, 30, 40, 50, 60, 70, 100 or more, for example such as those shown below in Tables 3-6 and further described in more detail below. Suitable log2FoldChange and TPM values may vary even further depending on tissue type specificities depending on the abundance/absence of good markers.

Applying the tissue specificity algorithms described above to identify surface markers, after adhesion selection and passaging, the TAF-MSCs cells may express various identified surface markers as shown below in Table 1, indicative of non-tissue specific TAF MSCs. One of skill in the art will understand that such surface markers may be present at various surface densities and may be upregulated or downregulated in comparison to other cell types. Therefore, such surface markers may be used to identify and isolate particular cell types. In some instances, the surface markers listed in Table 1 below may be at least 8-fold more highly expressed for TAF MSCs on average compared to other MSC cell types, particularly as compared to adult MSCs derived from bone marrow or adipose tissue. The thresholds used to generate Table 1 are as follows: X was selected as 15%, Y was selected as 50%, Z was selected as 8-fold and a TPM of more 3000 was selected. One of skill in the art will understand that the numbering used in Table 1 and all tables herein is merely used to indicate a total number of identified markers and not to indicate that one particular marker is more strongly expressed and/or preferred compared to another marker.

TABLE 1

| 1. TBC1D3K | TBC1 domain family member 3K |
| 2. AIF1L | allograft inflammatory factor 1 like |
| 3. CDHR1 | cadherin related family member 1 |
| 4. NKAIN4 | sodium/potassium transporting ATPase interacting 4 |
| 5. ABCB1 | ATP binding cassette subfamily B member 1 |
| 6. PLVAP | plasmalemma vesicle associated protein |
| 7. MSLN | mesothelin |
| 8. L1CAM | L1 cell adhesion molecule |
| 9. HAVCR1 | hepatitis A virus cellular receptor 1 |
| 10. MAL2 | mal, T cell differentiation protein 2 (gene/pseudogene) |
| 11. SLAMF7 | SLAM family member 7 |
| 12. DOC2B | double C2 domain beta |
| 13. ESAM | endothelial cell adhesion molecule |
| 14. GABRBI | gamma-aminobutyric acid type A receptor beta1 subunit |
| 15. CDH16 | cadherin 16 |
| 16. IGSF3 | immunoglobulin superfamily member 3 |
| 17. DSC3 | desmocollin 3 |
| 18. RHEX | regulator of hemoglobinization and erythroid cell expansion |
| 19. KCNIP 1 | potassium voltage-gated channel interacting protein 1 |
| 20. CD70 | CD70 molecule |
| 21. GFRA1 | GDNF family receptor alpha 1 |
| 22. CRB3 | crumbs cell polarity complex component 3 |
| 23. CLDN1 | claudin 1 |
| 24. AC 118754.1 | novel transcript |
| 25. SCN5A | sodium voltage-gated channel alpha subunit 5 |
| 26. FGFR4 | fibroblast growth factor receptor 4 |
| 27. KCNK3 | potassium two pore domain channel subfamily K member 3 |

TABLE 1-continued

| 28. DYSF | dysferlin |
| 29. EFNA1 | ephrinA1 |
| 30. KCNJ16 | potassium inwardly rectifying channel subfamily J member 16 |
| 31. MARCHF1 | membrane associated ring-CH-type finger 1 |
| 32. SYTL 1 | synaptotagmin like 1 |
| 33. CLSTN2 | calsyntenin 2 |
| 34. ITGB4 | integrin subunit beta 4 |
| 35. VAMP8 | vesicle associated membrane protein 8 |
| 36. GPRC5C | G protein-coupled receptor class C group 5 member C |
| 37. CD24 | CD24 molecule |
| 38. CELSR2 | cadherin EGF LAG seven-pass G-type receptor 2 |
| 39. CDH8 | cadherin 8 |
| 40. GRIP1 | glutamate receptor interacting protein 1 |
| 41. DMTN | dematin actin binding protein |
| 42. F11R | F11 receptor |
| 43. CADM1 | cell adhesion molecule 1 |
| 44. CDH6 | cadherin 6 |
| 45. F2RL2 | coagulation factor II thrombin receptor like 2 |
| 46. LYPD1 | LY6/PLAUR domain containing 1 |
| 47. SLC6A6 | solute carrier family 6 member 6 |
| 48. DSG2 | desmoglein 2 |
| 49. ADGRG1 | adhesion G protein-coupled receptor G 1 |
| 50. CCKAR | cholecystokinin A receptor |
| 51. OXTR | oxytocin receptor |
| 52. ITGA3 | integrin subunit alpha 3 |
| 53. AMIGO2 | adhesion molecule with Ig like domain 2 |
| 54. CELSR1 | cadherin EGF LAG seven-pass G-type receptor 1 |
| 55. EPHB2 | EPH receptor B2 |

As will be understood by one of skill in the art, suitable combinations of the markers listed in Table 1 may be used to separate TAF-MSCs from adult MSCs by selecting for specific markers from Table 1 or combinations of two, three, four, five, six or more markers from Table 1. In certain examples, TAF MSCs can be more specifically identified by identifying a combination of stronger expression, such as 8-fold or more stronger expression of any combination of the foregoing markers, e.g., TBC1D3K and/or AIF1L and/or CDHR1 and/or NKAIN4 and/or ABCB1 and/or PLVAP as compared to adult MSCs. When using combinations of markers, identification may be achieved with a lower threshold of stronger expression, such as 2-fold or more, 4-fold or more, or 6-fold or more expression of each of the markers.

In contrast to the above surface markers that may be more strongly expressed on the surface of TAF-MSCs (positive markers) compared to adult MSCs, in certain examples, the below surface markers in Table 2 may be more weakly expressed on TAF-MSCs as compared to other cell types (negative markers), such as ⅛-fold or less expression (optionally with TPM threshold>500) of any combination of the foregoing markers versus adult MSCs: IL13RA2, CLU, TMEM119, CEMIP, and LSP1. When using combinations of negative markers, identification may be achieved with a lower threshold of weaker expression, such as ½-fold or less, ¼-fold or less, or ⅙-fold or less expression of each of the markers.

Combinations of two or more these negative markers can also be used to more specifically isolate TAF MSCs. In addition, those skilled in the art will also recognize that combinations including both negative and positive markers, such as at any of the thresholds described above, can also be effective to more specifically isolate TAF MSCs.

TABLE 2

| 1. IL13RA2 | Interleukin-13 receptor subunit alpha-2 |
| 2. CLU | Clusterin |
| 3. TMEM119 | Transmembrane Protein 119 |

TABLE 2-continued

| | | |
|---|---|---|
| 4. | CEMIP | Cell Migration Inducing Hyaluronidase 1 |
| 5. | LSP1 | Lymphocyte Specific Protein 1 |
| 6. | GPNMB | Glycoprotein Nmb |
| 7. | FAP | Fibroblast Activation Protein Alpha |
| 8. | CRLF1 | Cytokine Receptor Like Factor 1 |
| 9. | MME | Membrane Metalloendopeptidase |
| 10. | CLMP | CXADR Like Membrane Protein |
| 11. | BGN | Biglycan |
| 12. | DDR2 | Discoidin Domain Receptor Tyrosine Kinase 2 |

Marker-Bused Selection

Amniotic fluid contains heterogenous cells in a homogenous fluid. Hence, a marker-based selection may be needed. One example of marker-based selection is via the use of Fluorescence activated cell sorting (FACS). Fluorescence activated cell sorting (FACS) may be used to purify the cell population of TAF-MSCs, FACS allows for a very high purity of the desired cell population, even when the target cell type expresses very low levels of identifying markers and/or separation is needed based on differences in marker density. FACS allows the purification of individual cells based on size, granularity and fluorescence. As will be understood by one of skill in the art, FACS may be used to select for certain cell populations that express one cell surface marker more than another cell population and vice-versa. In some examples of methods of purification, bulk methods of purification such as panning, complement depletion and magnetic bead separation, may be used in combination with FACS or as an alternative to FACS. In brief, to purify cells of interest via FACS, they are first stained with fluorescently-tagged monoclonal antibodies (mAbs), which recognize specific surface markers on the desired cell population. Negative selection of unstained cells may also allow for separation. For GMP production of cells according to some examples, FACS may be run using a closed system sorting technology such as MACSQuant® Tyto®. Samples may be kept contamination-free within the disposable, fully closed MACSQuant Tyto Cartridge. Further, filtered air may drive cells through a microchannel into the microchip at very low pressure (<3 PSI). However, before entering the microchannel, potential cell aggregates may be held back by a filter system guaranteeing a smooth sorting process. The fluorescence detection system may detect cells of interest based on predetermined fluorescent parameters of the cells. Based on their fluorescent and scatter light signatures, target cells may be redirected by a sort valve located within the microchannel. For certain examples of methods of purification, the success of staining and thereby sorting may depend largely on the selection of the identifying markers and the choice of mAh. Sorting parameters may be adjusted depending on the requirement of purity and yield. Unlike on conventional droplet sorters, cells sorted by the MACSQuant Tyto may not experience high pressure or charge, and may not get decompressed. Therefore, such a gentle sorting approach may result in high viability and functionality of cells. Alternatively, other marker-based selection techniques may be known to the skilled person and employed here. These include, but are not limited to, Magnetic-activated cell sorting, Microfluidic based sorting, Buoyancy activated cell sorting, mass cytometry etc.

Lung TAF Cell Markers

As explained above, analysis of RNAseq data from TAF-MSC clones, adult and neonatal MSC reference material as well as fetal fibroblasts and publicly available expression datasets may be used to identify and characterize TAF-MSC cells. For example, sub-populations of TAF-MSCs may be established by clustering their expression data (RNAseq) with neonatal reference samples. Such sub-populations include, but are not limited to, lung MSC, urinary tract MSC (described also as kidney MSCs in the present disclosure), and skin MSC. Gene lists of highly and lowly expressed genes for each cluster of expression data may allow for identification of surface maker genes for each cluster. Using such data comparison, sub-populations of TAF cells were compared to adult MSC cells based on their gene expressions (RNAseq) resulting in a list of neonatal-specific surface marker genes for each cluster. A number of surface markers of interest associated with lung TAF cells were identified. For example, a non-exclusive list of preferred surface markers used to identify and separate lung TAF cells are provided below. Moreover, as the number of different MSC-subtypes in TAF is limited, the selection of the tissue specific MSC may be done by firstly characterization, thereafter a stepwise negative selection/sorting of the material by taking into account the combined (multivariate) surface marker profile of the different tissue specific MSC's. One of skill in the art will understand that any such combination of these surface markers may be used for identifying and isolation of lung TAF cells from the general population of TAF-derived cells and/or TAF-MSC cells. In some examples, the below non-exclusive list of surface markers may be more highly expressed on the surface of Lung-TAF cells as compared to other cell types, such as other TAF-derived cells and/or TAF-MSC cells.

As explained above, bioinformatics techniques may be used to identify tissue-specific surface markers, therefore, the surface markers identified in Table 3 may have at least a 10-fold increase in expression on prioritized clones compared to the average TAF-MSC clone (optionally with TPM threshold>2000).

TABLE 3

| | |
|---|---|
| 1. | PCDH19—protocadherin 19; |
| 2. | DDR1—discoidin domain receptor tyrosine kinase 1; |
| 3. | MME—membrane metalloendopeptidase; |
| 4. | IFITM10—interferon induced transmembrane protein 10; |
| 5. | BGN—biglycan; |
| 6. | NOTCH3—notch receptor 3; |
| 7. | SULF1—sulfatase 1; |
| 8. | TNFSF18—TNF superfamily member 18; |
| 9. | BDKRB1—bradykinin receptor Bl; |
| 10. | FLT1—fm s related tyrosine kinase 1; |
| 11. | PDGFRA—platelet derived growth factor receptor alpha; |
| 12. | TNFSF4—TNF superfamily member 4; |
| 13. | UNC5B—unc-5 netrin receptor B; |
| 14. | FAP—fibroblast activation protein alpha; |
| 15. | CASP1—caspase 1; |
| 16. | CD248—Endosialin; |
| 17. | DDR2—discoidin domain receptor tyrosine kinase 2; |
| 18. | PCDH18—protocadherin 18; and/or |
| 19. | CRLF1—cytokine receptor like factor 1; |

In contrast to the above surface markers that may be more strongly expressed on the surface of lung TAF MSCs, in certain examples, the below surface markers may be more weakly expressed on lung TAF MSCs as compared to other cell types, such as other TAF-derived cells and/or TAF-MSCs: CD24, ITGB4, TNFSF10, GFRA1, CD74, FGFR4, HAVCR1, and OSCAR. As will be understood by one of skill in the art, one, two, three, four, or more of the aforementioned more weakly expressed surface markers may be used to separate lung TAF cells from other cell types such as other TAF-derived cells and/or TAF-MSCs.

In certain examples, the cell surface marker CD248 (Endosialin) may be used to sort lung TAF MSCs from a population of TAF MSCs. Further surface markers that may be used to sort lung TAF MSCs include DDR-1 (discoidin domain receptor tyrosine kinase 1) as well as LRRC38 (Leucine Rich Repeat Containing Protein 38), all three of which have been identified via antibodies as useful markers for separation. In some examples, Endosialin, DDR-1, and/or LRRC38 alone or in combination with other markers may be used to sort. Endosialin may be combined with DDR-1 or LRRC38 to sort, or DDR-1 and LRRC38 may be combined without Endosialin.

As will be understood by one of skill in the art, suitable combinations of the markers listed in Table 3 and CD248, DDR1, and LRRC38 may be used to separate lung TAF MSCs from TAF MSCs by selecting for specific markers from Table 3 or combinations of two, three, four, five, six or more markers from Table 3 and/or CD248 and/or DDR1 and/or FRR38. In certain examples, lung TAF MSCs can be more specifically identified by identifying a combination of stronger expression, such as 10-fold or more stronger expression (optionally with TPM threshold>2000) of any combination of the foregoing markers, e.g., PCDH19 and/or DDR1 and/or MME and/or IFITM10 and/or BGN and/or NOTCH3 and/or CD248 and/or DDR-1 and/or FRR38 as compared to TAF MSCs. When using combinations of markers, identification may be achieved with a lower threshold of stronger expression, such as 4-fold or more, 6-fold or more, or 8-fold or more expression of each of the markers.

In contrast to the above surface markers that may be more strongly expressed on the surface of lung TAF MSCs (positive markers) compared to TAF MSCs, in certain examples, the below surface markers may be more weakly expressed on lung TAF-MSCs as compared to other cell types (negative markers), such as ⅛-fold or less expression (optionally with TPM>500) of any combination of the foregoing markers versus TAF MSCs: ACE2, CD24, ITGB4, TNFSF10, GFRA1, CD74, FGFR4, HAVCR1, and OSCAR. When using combinations of negative markers, identification may be achieved with a lower threshold of weaker expression, such as ½-fold or less, ¼-fold or less, or ⅙-fold or less expression of each of the markers. ACE2 is of particular interest, because, as described above, ACE2 is the primary surface protein for attachment of SARS-CoV-2 potentially leading to COVID-19 infection. Therefore, cells with less ACE2 surface proteins may be more resistant to infection by SARS-CoV-2.

Combinations of two or more these negative markers can also be used to more specifically isolate lung TAF MSCs. In addition, those skilled in the art will also recognize that combinations including both negative and positive markers, such as at any of the thresholds described above, can also be effective to more specifically isolate lung TAF MSCs.

Treatment of Respiratory Disease

Lung TAF MSCs, such as those described herein this section and elsewhere in the specification, may be uniquely suited for the treatment of COVID-19 patients with ARDS as well as patients with other viral/bacterial/environmental causes of ARDS. As described elsewhere herein, Lung TAF MSCs may be suitable for the treatment of a variety of acute and/or chronic respiratory diseases. Additionally, Lung TAF MSCs and TAF MSCs generally are also known to be smaller than conventional MSCs, thereby making them more suitable for intravenous dosed treatments. "Morphology and size of stem cells from mouse and whale: observational study" by Hoogdujin et al. and "The size of mesenchymal stem cells is a significant cause of vascular obstructions and stroke." by Ge et al. provide further details regarding the relative size of MSCs and their potential reduced role in vascular obstructions or stroke.

For example, Lung TAF MSCs may have an anti-inflammatory effect on other cell types, such as cells found within various organs and tissues such as the lung. Therefore, incorporation of Lung TAF MSCs within the lung of a patient suffering from an acute and/or chronic respiratory disease may reduce inflammation. Lung TAF MSCs may be particularly beneficial to patients suffering from ARDS caused by COVID-19 because the Lung TAF MSCs may reduce the magnitude of the dangerous "cytokine storm" induced in COVID-19 patients. Additionally, in some examples, Lung TAF MSCs express lower levels of the ACE/ACE2 receptor as compared to adult bone marrow and adipose MSCs, indicating that SARS-CoV-2 may be less likely to infect Lung TAF MSCs as compared to other MSCs. Further, TAF MSCs (including lung TAF MSCs) have been shown to reduce cytokine responses such as IL-6, IL-18 and TNF-a etc., as well as generally lower the activation and proliferation of lymphocytes (T-cell, macrophages etc) and increase levels of several growth factors.

FIGS. 17A-17D show an example of the results from a proof-of-principle study on the potential use of Lung TAF MSCs for treatment, performed using neonatally sorted TAF MSCs expressing MSC lung cell surface markers including CD248, DDR1, and LRRC38 (called "LBX-THX-001 cells"). The purpose of the study was to investigate the effects of LBX-THX-001 cells in a bleomycin induced lung fibrosis model in male rats. Two cell concentrations (2 M cell/kg and 5 M cells/kg) and two types of vehicles for the cells were tested (PBS and CryoStor CS-10).

The development of fibrosis in rat lung after exposure to bleomycin is well documented in the literature and a frequently used model for studying the pathology of lung fibrosis and also the effect of different treatments. The number of LBX-THX-001 cells injected were chosen to be relevant for a possible human therapy. The number of cells were therefore chosen to reflect cell numbers used in previous studies on rats (8-20 M cells/kg) and humans (0.5-2 M cells/kg).

An intra-tracheal instillation of bleomycin (1000 U/rat) to 34 male SD-rats was used to induce lung fibrosis in the rats. During the first week, the rats were monitored and weighed daily and thereafter twice/week until termination of the study. At day 4 post bleomycin challenge, the LBX-THX-001 cells were administered by an intra-venous (i.v.) injection. The injection volume was 194-535 µL (maximal tolerated injection volume 1 mL/kg). The response to the intra-tracheal instillation of bleomycin was as expected based on previous experience for the model with weight loss during the first days after instillation and thereafter recovery. There were no significant differences in weight loss between the bleomycin group and the treatment groups.

As shown in FIGS. 17A-D, bleomycin instillation induced fibrotic change in the lung. The histopathological evaluation concluded pathological changes in the bleomycin group both with regard to percent of parenchyma affected and after scoring using the modified Ashcroft scale. As shown in FIGS. 17A-D, the group treated with LBX-THX-001 cells (2 million cells/kg) 4 days post Bleomycin showed significantly less fibrosis in their lungs compared to the bleomycin group. This was seen both in the histopathological evaluation using the read-out "percent parenchyma affected" (FIGS. 17A-B) and the fibrosis scoring Ashcroft modified scale (FIGS. 17A-D). No human MSCs could be detected in rat lungs at termination (after 28 days). The results of this proof-of-principle study demonstrate that treatment via lung TAF MSCs improved lung recovery outcomes, therefore such cells may be highly relevant for respiratory disease such as SARS and COVID-19 induced acute respiratory distress syndrome (RDS), interstitial pneumonia, and sepsis.

Figure 18:
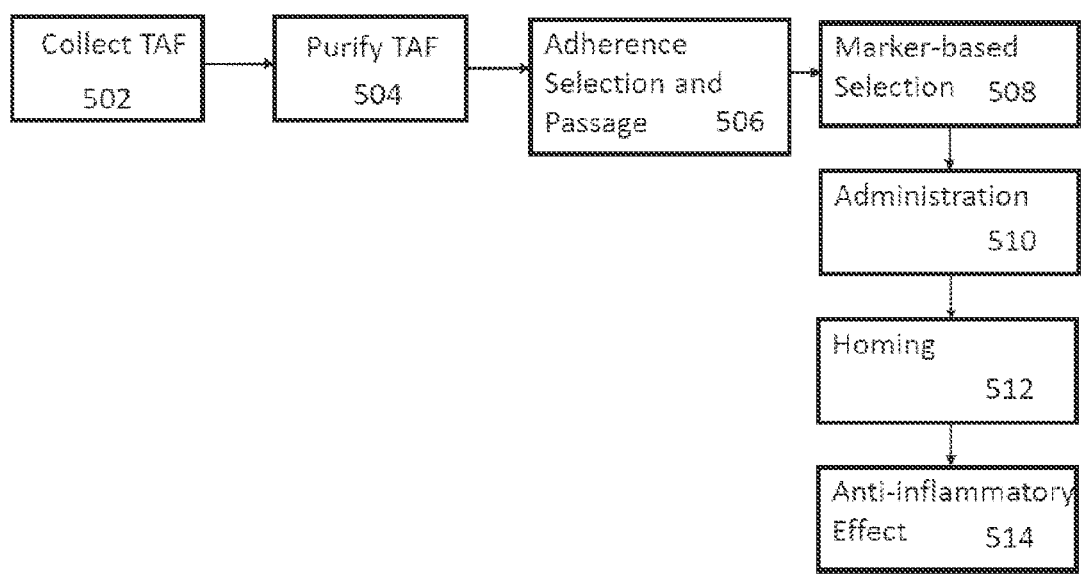
FIG. 18 is a flow chart of a method for treating acute respiratory distress syndrome according to an example.

FIG. 18 depicts a method 500 for the treatment of patients with ARDS (such as caused by COVID-19) or any other suitable acute or chronic respiratory disease. In the first step 502, TAF is collected such as described elsewhere herein. The TAF is then purified 504 by a suitable method to remove particulate matter and obtain purified TAF cells, such as described elsewhere in the specification. The TAF cells are then subjected to adherence selection 506 such as described elsewhere herein to obtain TAF adherence cells, which are then then passaged such as described elsewhere herein to generate TAF MSCs. The TAF MSCs may then be subjected to any suitable marker-based selection 508 method such as described elsewhere herein (for example, FACS) to obtain Lung TAF MSCs. In some examples, the Lung TAF MSCs may be selected based upon the presence of CD248 (Endosialin) alone or in combination with any of the lung markers identified herein.

Once the Lung TAF MSCs have been identified, they may be administered to a patient suffering from an acute or chronic respiratory disease (such as COVID-19 induced ARDS). Administration may be via any suitable method, for example via intravenous drip or spray. MSCs (such as Lung TAF MSCs) are well known to home to the appropriate organ and/or tissue, therefore after administration the Lung TAF MSCs will home to the lung. For the intravenous drip, the Lung TAF MSCs may be suspended in any suitable fluid, such as normal saline, for example about 25 ml, 50 ml, 100 ml, 150 ml, 200 ml, 250 ml, or 300 ml of saline. The total number of cells to be administered may range from about 500,000 to 8,000,000 cells per kg (kg of patient), about 1,000,000 to 6,000,000 cells per kg, or about 2,000,000 to 4,000,000. In certain examples, 1,000,000 cells per kg patient may be administered. The window period for Lung TAF MSCs transplantation may be any suitable time, or example after diagnosis, before diagnosis if risk factors indicate a benefit for treatment, and/or once symptoms are worsening even while undergoing other treatment. Administration of the cells may be performed over the course of approximately about 10-60 minutes, such as about 20-50 minutes, about 30-40 minutes or about 40 minutes. The speed of administration may be about 10, 20, 30, 40, 50, 60, 70, or more drops per minute. Administration of the cells may involve multiple treatments, such as 1, 2, 3, 4, 6, 8 or 10 or more injections over a suitable time frame such as over the course of 8 hours, 24 hours, 2 days, 4 days, 7 day, 14 days or more than 14 days. Once the Lung TAF MSCs have been administered intravenously (or via any suitable method), the Lung TAF MSCs home to the lungs of the patient as explained in "Mesenchymal Stem Cell-Based Therapy of Inflammatory Lung Diseases: Current Understanding and Future Perspectives" by Harrell et al. In some examples, once the Lung TAF MSCs are introduced to the lung, the Lung TAF MSCs may reduce inflammation 514 in the lung and aid in repairing damaged tissue. The reduction in inflammation may reduce the magnitude of ARDS and potentially reduce the mortality rate of patients infected with COVID-19.

Additional Terminology and Definitions

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing examples. The disclosure extends to any novel one, or any novel combination, of the features disclosed in this specification (including any accompanying claims, abstract and drawings), or to any novel one, or any novel combination, of the steps of any method or process so disclosed.

Those skilled in the art will appreciate that in some examples, the actual steps taken in the processes illustrated or disclosed may differ from those shown in the figures. Depending on the example, certain of the steps described above may be removed, others may be added. For example, the actual steps or order of steps taken in the disclosed processes may differ from those shown in the figure. Depending on the example, certain of the steps described above may be removed, others may be added. Furthermore, the features and attributes of the specific examples disclosed above may be combined in different ways to form additional examples, all of which fall within the scope of the present disclosure.

Conditional language, such as "can," "could," "might," or "may," unless specifically stated otherwise, or otherwise understood within the context as used, is generally intended to convey that certain examples include, while other examples do not include, certain features, elements, or steps. Thus, such conditional language is not generally intended to imply that features, elements, or steps are in any way required for one or more examples or that one or more examples necessarily include logic for deciding, with or without user input or prompting, whether these features, elements, or steps are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise, the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z Thus, such conjunctive language is not generally intended to imply that certain examples require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated. amount. As another example, in certain examples, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1. degree.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain examples of the disclosure are encompassed in the claim set listed below or presented in the future.

What is claimed is:

1. A method of treating acute respiratory distress syndrome in a patient in need thereof, comprising:
    performing adherence selection on term amniotic fluid (TAF) cells to obtain TAF adherence cells;
    passaging the TAF adherence cells to obtain TAF mesenchymal stem cells (TAF MSCs);
    selecting TAF MSCs that express Endosialin to obtain lung TAF MSCs; and
    administering the lung TAF MSCs to the patient.

2. The method of claim 1, wherein selecting TAF MSCs to obtain Lung TAF MSCs further comprises selecting TAF MSCs that express DDR1.

3. The method of claim 1, wherein selecting TAF MSCs to obtain Lung TAF MSCs further comprises selecting TAF MSCs that express LRRC38.

4. The method of claim 1, wherein selecting TAF MSCs to obtain lung TAF MSCs further comprises selecting TAF MSCs that express a Group A surface marker selected from the group consisting of PCDH19, DDR1, MME, IFITM10, BGN, NOTCH3, SULF1, TNFSF18, BDKRB1, FLT1, PDGFRA, TNFSF4, UNC5B, FAP, CASP1, CD248, DDR2, PCDH18, LRRC38, and CRLF1.

5. The method of claim 1, wherein selecting lung TAF MSCs further comprises excluding TAF MSCs that express a Group B surface marker selected from the group consisting of CD24, ITGB4, TNFSF10, GFRA1, CD74, FGFR4, HAVCR1, and OSCAR.

6. The method of claim 1, wherein the lung TAF MSCs are administered at a concentration of about 1-2 million cells per kg of body weight of the patient.

7. The method of claim 1, wherein administering the lung TAF MSCs comprises administering the lung TAF MSCs via an intravenous drip.

8. The method of claim 7, wherein the intravenous drip comprises about 40 drops per minute.

* * * * *